(12) United States Patent
Imamura et al.

(10) Patent No.: US 7,183,278 B1
(45) Date of Patent: Feb. 27, 2007

(54) PICOLINAMIDE DERIVATIVE AND HARMFUL ORGANISM CONTROL AGENT COMPRISING SAID PICOLINAMIDE DERIVATIVE AS ACTIVE COMPONENT

(75) Inventors: Keiichi Imamura, Tokyo-To (JP); Kouichi Mitomo, Odawara (JP); Natsuko Yamada, Yokohama (JP); Kazumi Yamamoto, Yokohama (JP); Takashi Teraoka, Yokohama (JP); Osamu Sakanaka, Odawara (JP); Hiroshi Kurihara, Yokohama (JP); Makoto Taniguchi, Kishiwada (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 09/830,923

(22) PCT Filed: Nov. 4, 1999

(86) PCT No.: PCT/JP99/06142

§ 371 (c)(1),
(2), (4) Date: Aug. 9, 2001

(87) PCT Pub. No.: WO00/26191

PCT Pub. Date: May 11, 2000

(30) Foreign Application Priority Data

Nov. 4, 1998  (JP) ................................ 10-313688

(51) Int. Cl.
*A61K 31/535* (2006.01)
*A61K 31/44* (2006.01)
*A61K 31/497* (2006.01)
*C07D 401/00* (2006.01)

(52) U.S. Cl. .................. 514/232.2; 514/348; 514/350; 514/342; 514/340; 514/253.01; 546/296; 546/272.4; 546/271.4; 546/298; 544/405; 544/106

(58) Field of Classification Search ................ 546/292, 546/291, 296, 298, 272.4, 271.4; 514/346, 514/348, 350, 232.2, 342, 340, 253.01; 544/106, 544/405
See application file for complete search history.

(56) References Cited

U.S. PATENT DOCUMENTS

| | | | | |
|---|---|---|---|---|
| 3,228,950 | A | * 1/1966 | Renk et al. | ............ 546/291 |
| 3,354,145 | A | * 11/1967 | Baumann et al. | .......... 540/327 |
| 4,005,075 | A |  1/1977 | Yamada et al. | |
| 4,101,507 | A |  7/1978 | Lohr, Jr. | |
| 4,125,611 | A | 11/1978 | Yamade et al. | |
| 4,293,649 | A | 10/1981 | Hoehn et al. | |
| 5,607,926 | A | * 3/1997 | Hecker et al. | |
| 5,641,778 | A |  6/1997 | Maibaum et al. | |
| 5,658,933 | A |  8/1997 | Weidmann et al. | |
| 6,355,660 | B1 | * 3/2002 | Ricks et al. | ................ 514/357 |

FOREIGN PATENT DOCUMENTS

| | | |
|---|---|---|
| EP | 0 266 950 | 5/1988 |
| EP | 0528172 | * 2/1993 |
| EP | 566138 | 10/1993 |

(Continued)

OTHER PUBLICATIONS

Ca 127:81061, "Influence of steric crowding on the electrochemical reduction of substituted tertiary pyridylcarboxamides in aqueou acidic medium", Largeron et.al., 1997, p. 3.*

(Continued)

*Primary Examiner*—Thomas McKenzie
*Assistant Examiner*—Binta Robinson
(74) *Attorney, Agent, or Firm*—Wenderoth, Lind & Ponack, L.L.P.

(57) ABSTRACT

Disclosed are novel compounds useful for the control of harmful organisms, harmful organism control agents using the same, and processes for producing the novel compounds. The useful novel compounds according to the present invention include compounds represented by formula (1). The compounds represented by formula (1) have potent activity against harmful organisms, and do not have phytotoxicity against agricultural and gardening plants, as objects to which the compounds of the present invention are applied for preventive and exterminating purposes, and human beings and beasts

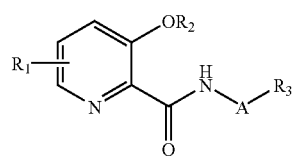

(1)

wherein A represents a bond or an optionally substituted alkylene chain; $R_1$ represents one or more groups, which may be the same or different, selected from the group consisting of a hydrogen atom, alkoxy, and haloalkoxy; $R_2$ represents a hydrogen atom, benzyl, alkyl or alkanoyl, in which the groups other than the hydrogen atom may be substituted; and $R_3$ represents a hydrogen atom, cycloalkyl, cycloalkenyl, aryl or a heterocyclic group, in which the groups other than the hydrogen atom may be substituted, excluding the case where $R_1$ represents a hydrogen atom, A represents a bond or a methylene chain, and $R_3$ represent phenyl or cyclohexyl, and the case where A represents an alkylene chain and $R_3$ represents a hydrogen atom.

19 Claims, No Drawings

FOREIGN PATENT DOCUMENTS

| | | |
|---|---|---|
| JP | 53-146758 | 12/1978 |
| JP | 6-25199 | 2/1994 |
| JP | 7-224039 | 8/1995 |
| JP | 8-231485 | 9/1996 |
| JP | 9-510471 | 10/1997 |
| WO | 95/25823 | 9/1995 |
| WO | WO 96/41795 | 12/1996 |
| WO | 19958166 A1 * | 12/2000 |
| WO | WO 01/14339 | 3/2001 |

OTHER PUBLICATIONS

Ca 125:301567, "Relationship between pyridine nitrogen basicity and steric crowding in an N-substituted-3-methoxypicolinamide series.", Largeron et. al., 1996, p. 3.*

Deacon, J. W., Modern Mycology, Third edition, 1997, p. 188.*

Largeron et. al., "Relationship between Pyridine Nitrogen Basicity and Steric Crowding in an N-substituted-3-methoxypicolinam Series", pp. 454-455, 1996, J. Chem. Research (S).*

Largeron et al., "Relationship Between Pyridine Nitrogen Basicity and Steric Crowding in an N-Substituted-3-methoxypicolinamide Series", J. Chem. Research (s), p. 454-455 (1996).

Margeron et al., "Electrochemical Reduction of Pristrin amycin IA and Related Streptogramins in Aqueous Acidic Medium", Tetrahedron, vol. 50, No. 21, p. 6307-6332 (1994).

French et al., "α-(N)-Formylheteroaromatic Thiosemicarbazones. Inhibition of Tumor-Derived Ribonucleoside Diphosphate Reductase and Correlation with In Vivo Antitumor Activity.", J. Med. Chem., vol. 17, No. 2, p. 172-181 (1974).

Nedenskov et al., "O-Alkylation of 3-pyridinols", Acta Chem. Scand., vol. 23, p. 1791-1796 (1969).

Largeron et al., "Relationship Between Pyridine Nitrogen Basicity and Steric Crowding in an N-Substituted-3-methoxypicolinamide Series", J. Chem. Research (s), p. 454-455 (1996).

Largeron et al., "Electrochemical Reduction of Pristin amycin IA and Related Streptogramins in Aqueous Acidic Medium", Tetrahedron, vol. 50, No. 21, p. 6307-6332 (1994).

French et al., "α-(N)-Formylheteroaromatic Thiosemicarbazones. Inhibition of Tumor-Derived Ribonucleoside Diphosphate Reductase and Correlation with In Vivo Antitumor Activity.", J. Med. Chem., vol. 17, No. 2, p. 172-181 (1974).

Nedenskov et al., "O-Alkylation of 3-pyridinols", Acta Chem. Scand., vol. 23, p. 1791-1796 (1969).

Largeron et al., "Relationship Between Pyridine Nitrogen Basicity and Steric Crowding in an N-Substituted-3-methoxypicolinamide Series", J. Chem. Research (s), p. 454-455 (1996).

Margeron et al., "Electrochemical Reduction of Pristin amycin IA and Related Streptogramins in Aqueous Acidic Medium", Tetrahedron, vol. 50, No. 21, p. 6307-6332 (1994).

French et al., "α-(N)-Formylheteroaromatic Thiosemicarbazones. Inhibition of Tumor-Derived Ribonucleoside Diphosphate Reductase and Correlation with In Vivo Antitumor Activity.", J. Med. Chem., vol. 17, No. 2, p. 172-181 (1974).

Nedenskov et al., "O-Alkylation of 3-pyridinols", Acta Chem. Scand., vol. 23, p. 1791-1796 (1969).

Patent Abstracts of Japan, vol. 1996, No. 1, Jan. 31, 1996, and JP 7 233165A, Sep. 5, 1995, Abstract (1 pg).

* cited by examiner

PICOLINAMIDE DERIVATIVE AND HARMFUL ORGANISM CONTROL AGENT COMPRISING SAID PICOLINAMIDE DERIVATIVE AS ACTIVE COMPONENT

This application is a 371 application of PCT/JP99/06142, filed Nov. 4, 1999.

BACKGROUND OF THE INVENTION

1. Field of the Invention

The present invention relates to a useful novel picolinamide derivative, a harmful organism control agent comprising said picolinamide derivative as an active component, and use thereof. The present invention also relates to a picolinic acid derivative as an intermediate indispensable for synthesizing a picolinamide derivative, and a process for producing the same.

2. Background Art

Certain picolinamide derivatives are disclosed in Japanese Patent Laid-Open No. 242635/1995. This publication, however, does not disclose the use of the picolinamide derivatives as a harmful organism control agent. Further, the appearance of fungi resistance to existing various plant pathogenic fungi control agents has lead to an ever-increasing demand for novel plant pathogenic fungi control agents.

SUMMARY OF THE INVENTION

The present inventors have found that a novel picolinamide derivative has potent activity against harmful organisms and, at the same time, is highly safe against plants as a control object. The present invention has been made based on such finding.

Accordingly, it is an object of the present invention to provide a novel picolinamide derivative useful for the control of harmful organisms, and to provide a harmful organism control agent comprising the novel picolinamide derivative as an active component.

According to one aspect of the present invention, there is provided a picolinamide derivative represented by formula (1):

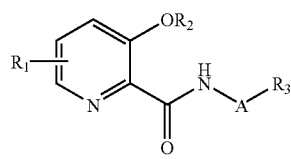

(1)

wherein

A represents a bond or an optionally substituted alkylene chain;

$R_1$ represents one or more groups, which may be the same or different, selected from the group consisting of a hydrogen atom, alkoxy, and haloalkoxy;

$R_2$ represents a hydrogen atom, benzyl, alkyl or alkanoyl, in which the groups other than the hydrogen atom may be substituted; and $R_3$ represents a hydrogen atom, cycloalkyl, cycloalkenyl, aryl or a heterocyclic group, in which the groups other than the hydrogen atom may be substituted, excluding the case where $R_1$ represents a hydrogen atom, A represents a bond or a methylene chain, and $R_3$ represents phenyl or cyclohexyl, and the case where A represents an alkylene chain and $R_3$ represents a hydrogen atom.

According to another aspect of the present invention, there is provided, as an intermediate for the derivative represented by formula (1), a picolinic acid derivative represented by formula (2) or a salt thereof:

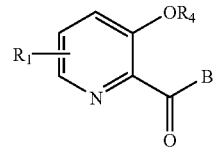

(2)

wherein

B represents hydroxyl, a halogen atom or alkoxy;

$R_1$ represents one or more groups, which may be the same or different, selected from the group consisting of $C_1$–$C_4$ alkoxy and $C_1$–$C_4$ haloalkoxy; and $R_4$ represents a hydrogen atom, benzyl, $C_1$–$C_4$ alkyl or $C_1$–$C_4$ alkanoyl, in which the groups other than the hydrogen atom may be substituted, excluding the case where $R_1$ represents 4-methoxy with $R_4$ representing hydrogen or benzyl.

DETAILED DESCRIPTION OF THE INVENTION

Picolinamide Derivative Represented by Formula (1)

In formula (1), A represents a bond or an optionally substituted alkylene chain. $R_1$ represents one, two or more groups, which may be the same or different, selected from the group consisting of a hydrogen atom, alkoxy and haloalkoxy. $R_2$ represents a hydrogen atom, benzyl, alkyl or alkanoyl, in which the groups other than the hydrogen atom may be substituted. $R_3$ represents a hydrogen atom, cycloalkyl, cycloalkenyl, aryl or a heterocyclic group, in which the groups other than the hydrogen atom may be substituted.

In this case, the picolinamide derivatives represented by formula (1), wherein the case where $R_1$ represents a hydrogen atom, A represents a bond or a methylene chain, and $R_3$ represents phenyl or cyclohexyl, or salts thereof, and the picolinamide derivatives represented by formula (1), wherein A represents an alkylene chain and $R_3$ represents a hydrogen atom, or salts thereof are excluded from the scope of the present invention.

A

The optionally substituted alkylene chain represented by A is preferably an alkylene chain having 1 to 12 carbon atoms, and specific preferred examples thereof include methylene chain, 1,1- or 1,2-ethylene chain, 1,1-, 1,2-, 1,3-, or 2,2-propylene chain, 2-methyl-1,3-propylene chain, 1,1-, 1,2-, 1,3-, 1,4-, 2,2-, 2,3-, or 2,4-butylene chain, 3,3-dimethyl-1,4-butylene chain, 1,1,3,3-tetramethyl-1,4-butylene chain, hexamethylene chain, heptamethylene chain, octamethylene chain, nonamethylene chain, decamethylene chain, undecamethylene chain, dodecamethylene chain, 1,5-pentyl chain and 2,5-dichloro-1,5-pentyl chain.

More preferred examples of A include a bond, methylene chain, 1,1- or 1,2-ethylene chain, 1,2-propylene chain, 1,3-propylene chain, 2,2-propylene chain, 1,4-butylene chain, 2,4-butylene chain, 3,3-dimethyl-1,4-butylene chain, 1,1,3,3-tetramethyl-1,4-butylene chain, hexamethylene chain, heptamethylene chain, octamethylene chain, 1,5-pentyl chain and 2,5-dichloro-1,5-pentyl chain.

$R_1$

Alkoxy or haloalkoxy represented by $R_1$ is preferably alkoxy or haloalkoxy having 1 to 4 carbon atoms, and specific preferred examples thereof include methoxy, ethoxy, 1-propyloxy, isopropyloxy, 1-butyloxy, 2-butyloxy, t-butyloxy, trifluoromethoxy, difluoromethoxy, fluoromethoxy, difluorochloromethoxy and trifluoroethoxy.

More preferred examples of $R_1$ include a hydrogen atom, 4-methoxy, 6-methoxy, 4,5-dimethoxy and 4,6-dimethoxy.

$R_2$

The substituted benzyl represented by $R_2$ is preferably p-nitrobenzyl or p-methoxybenzyl.

The alkyl represented by $R_2$ is preferably optionally substituted alkyl having 1 to 4 carbon atoms, and specific preferred examples thereof include methoxymethyl and methoxyethoxymethyl.

The alkanoyl represented by $R_2$ is preferably alkanoyl having 1 to 4 carbon atoms, and specific preferred examples thereof include isobutyryl, acetyl, propionyl and pivaloyl.

More preferred examples of $R_2$ include a hydrogen atom, benzyl, acetyl, and propionyl.

$R_3$

Cycloalkyl or cycloalkenyl represented by $R_3$ is preferably cycloalkyl having 3 to 12 carbon atoms or cycloalkenyl having 3 to 12 carbon atoms, and specific preferred examples thereof include cyclopropyl, cyclobutyl, cyclopentyl, cyclohexyl, cycloheptyl, cyclooctyl, cyclononyl, cyclodecyl, cycloundecyl, cyclododecyl, cyclohexenyl, tetrahydronaphthyl, decahydronaphthyl, cyclododecatrienyl, indanyl, norbornyl and adamantyl.

When cycloalkyl or cycloalkenyl represented by $R_3$ is substituted by a substituent, examples of substituents include a halogen atom, cyano, nitro, amino, carboxyl, hydroxyl, phenyl, which may be substituted by one, two or more substituents selected from the group consisting of a halogen atom, cyano, nitro, amino, alkylamino, alkanoylamino, $C_1$–$C_5$ alkyl atoms, $C_1$–$C_4$ haloalkyl, $C_1$–$C_4$ alkoxy, and $C_1$–$C_4$ haloalkoxy, $C_1$–$C_5$ alkyl $C_1$–$C_4$ haloalkyl, and $C_1$–$C_4$ haloalkoxy.

Specific examples of preferred substituents for cycloalkyl or cycloalkenyl represented by $R_3$ include a fluorine atom, a chlorine atom, a bromine atom, cyano, nitro, hydroxyl, carboxyl, methyl, ethyl, n-propyl, isopropyl, n-butyl, sec-butyl, isobutyl, t-butyl, n-pentyl, 2-pentyl, 3-pentyl, isopentyl, neopentyl, phenyl, methoxy, ethoxy, methoxycarbonyl and ethoxycarbonyl.

Aryl or heterocyclic group represented by $R_3$ is preferably a monocyclic or polycyclic 3- to 12-membered aryl, or 3- to 12-membered heterocyclic phenyl, and specific preferred examples thereof include phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolinyl, pyrimidinyl, pyridazinyl, pyrazinyl, oxiranyl, tetrahydrofuryl, perhydropyranyl, pyrrolidinyl, piperidinyl, homopiperidinyl and morpholinyl.

When aryl or heterocyclic group represented by $R_3$ is substituted by a substituent, the substituent may be one or two or more groups selected from the group consisting of:

a halogen atom, cyano, nitro, amino, hydroxyl, formyl, carboxyl, carbamoyl, or thiocarbamoyl;

alkyl, alkoxy, alkylthio, alkylsulfinyl, or alkylsulfonyl, wherein said groups are straight-chain or branched groups having 1 to 6 carbon atoms;

straight-chain or branched alkenyl or alkenyloxy having 2 to 6 carbon atoms;

haloalkyl, haloalkoxy, haloalkylthio, haloalkylsulfinyl, or haloalkylsulfonyl, wherein said groups are straight-chain or branched groups having 1 to 6 carbon atoms that each have 1 to 13 halogen atoms which may be the same or different;

straight-chain or branched $C_2$–$C_6$ haloalkenyl or straight-chain or branched $C_2$–$C_6$ haloalkenyloxy, wherein said groups each have 1 to 11 halogen atoms which may be the same or different;

acylamino, N-acyl-N-alkylamino, alkylamino, dialkylamino, alkylcarbonyl, alkylcarbonyloxy, alkoxycarbonyl, alkylsulfonyloxy, hydroxyiminoalkyl or alkoxyiminoalkyl, wherein said groups each have straight-chain or branched alkyl having 1 to 6 carbon atoms;

alkylene, dioxyalkylene, or polyoxyalkylene, wherein said groups may be substituted by one, two or more substituents selected from the group consisting of a halogen atom, straight-chain or branched alkyl having 1 to 4 carbon atoms, and straight-chain or branched haloalkyl having 1 to 5 carbon atoms, which has 1 to 11 halogen atoms which may be the same or different, and are present as a chain which is substituted in its both ends at adjacent positions on the ring to form a ring; and cycloalkyl having 3 to 6 carbon atoms, aryl, aryloxy, arylthio, arylsulfinyl, arylsulfonyl, arylamino, arylalkyl, arylalkyloxy, aryloxyalkyloxy, arylthioalkyloxy, aryloxyalkylthio, arylthioalkylthio, arylalkylthio, aryloxyalkyl, arylthioalkyl, heterocyclic group, heterocyclic oxy, heterocyclic thio, heterocyclic alkyl, heterocyclic alkyloxy or heterocyclic alkylthio, wherein alkyl present in these groups is straight-chain or branched alkyl having 1 to 5 carbon atoms.

A specific preferred example of the substituent for aryl or hetrocyclic group represented by $R_3$ is at least one group selected from the group consisting of:

a fluorine atom, a chlorine atom, a bromine atom, cyano, nitro, amino, hydroxyl, formyl, carboxyl, carbamoyl, thiocarbamoyl, methyl, ethyl, n-propyl, isopropyl, n-butyl, isobutyl, sec-butyl, t-butyl, n-pentyl, 2-pentyl, 3-pentyl, isopentyl, 2-methyl-1-butyl, neopentyl, methoxy, ethoxy, n-propoxy, isopropoxy, methylthio, ethylthio, n-propylthio, isopropylthio, methylsulfinyl, methylsulfonyl, ethylsulfinyl, ethylsulfonyl, trifluoromethyl, trifluoroethyl, trifluoromethoxy, difluoromethoxy, difluorochloromethoxy, trifluoroethoxy, difluoromethylthio, chlorodifluoromethylthio, trifluoromethylthio, trifluoromethylsulfinyl, trifluoromethylsulfonyl, acetylamino, formylamino, N-formyl-N-methylamino, methylamino, ethylamino, n-propylamino, isopropylamino, dimethylamino, diethylamino, acetyl, propionyl, acetoxy, methoxycarbonyl, ethoxycarbonyl, methylsulfonyloxy, ethylsulfonyloxy, hydroxyiminomethyl, hydroxyiminoethyl, methoxyiminomethyl, ethoxyiminomethyl, methoxyiminoethyl, and ethoxyiminoethyl;

trimethylene, tetramethylene, methylenedioxy, ethylenedioxy, and 1,4,7,10,13-pentoxatridecamethylene, wherein these groups may be substituted by one, two or more substituents selected from the group consisting of a fluorine atom, a chlorine atom, methyl, trifluoromethyl, ethyl, n-propyl and i-propyl, and are present as a chain which is substituted in its both ends at adjacent positions on the ring to form a ring; and cyclopropyl, cyclobutyl, cyclopentyl, cyclohexyl, phenyl, phenoxy, phenylalkyl, phenylthio, phenylsulfinyl, phenylsulfonyl, phenylcarbonyl, phenoxyalkyl, phenoxyalkyloxy, phenylthioalkyloxy, phenoxyalkylthio, phenylthioalkylthio, phenylthioalkyl, phenylalkyloxy, phenylalkylthio, pyridyl, pyridyloxy, pyridylthio, anilino, morpholinyl, and piperidyl, wherein alkyl chain present in these groups is straight-chain or branched alkyl chain having 1 to 4 carbon atoms.

According to a preferred embodiment of the present invention, if the substituent in the case where aryl or heterocyclic group represented by $R_3$ is the above-described substituent, that is, cycloalkyl having 3 to 6 carbon atoms, aryl, aryloxy, arylthio, arylsulfinyl, arylsulfonyl, arylamino, arylalkyl, arylalkyloxy, aryloxyalkyloxy, arylthioalkyloxy, aryloxyalkylthio, arylthioalkylthio, arylalkylthio, aryloxyalkyl, arylthioalkyl, heterocyclic group, heterocyclic oxy, heterocyclic thio, heterocyclic alkyl, heterocyclic alkyloxy or heterocyclic alkylthio, wherein alkyl chain present in these groups is straight-chain or branched alkyl chain having 1 to 5 carbon atoms, then these substituents are preferably substituted by an additional substituent. In this case, the additional substituent is one, two or more groups selected from the group consisting of:

a halogen atom, cyano, nitro, amino, hydroxyl, formyl, carboxyl, carbamoyl or thiocarbamoyl;

alkyl, alkoxy, alkylthio, alkylsulfinyl or alkylsulfonyl, wherein said groups are straight-chain or branched-chain groups having 1 to 6 carbon atoms;

straight-chain or branched $C_2$–$C_6$ alkenyl or straight-chain or branched $C_2$–$C_6$ alkenyloxy;

haloalkyl, haloalkoxy, haloalkylthio, haloalkylsulfinyl, or haloalkylsulfonyl, wherein said groups are straight-chain or branched groups having 1 to 6 carbon atoms that each have 1 to 13 halogen atoms which may be the same or different;

straight-chain or branched $C_2$–$C_6$ haloalkenyl or straight-chain or branched $C_2$–$C_6$ haloalkenyloxy, wherein said groups each have 1 to 11 halogen atoms which may be the same or different;

acylamino, N-acyl-N-alkylamino, alkylamino, dialkylamino, alkylcarbonyl, alkylcarbonyloxy, alkoxycarbonyl, alkylsulfonyloxy, hydroxyiminoalkyl, or alkoxyiminoalkyl, wherein said groups each have straight-chain or branched alkyl having 1 to 6 carbon atoms;

alkylene, dioxyalkylene or polyoxaalkylene, wherein said groups may be substituted by one or two or more substituents selected from the group consisting of a halogen atom, straight-chain or branched alkyl having 1 to 4 carbon atoms, straight-chain or branched haloalkyl having 1 to 5 carbon atoms, which has 1 to 11 halogen atoms which may be the same or different, and are present as a chain which is substituted in its both ends at adjacent positions on the ring to form a ring; and cycloalkyl having 3 to 6 carbon atoms or aryl, wherein said groups may be substituted by one or two or more substituents selected from the group consisting of a halogen atom, straight-chain or branched $C_1$–$C_4$ alkyl or straight-chain or branched $C_1$–$C_4$ alkoxy, and straight-chain or branched haloalkyl having 1 to 5 carbon atoms that has 1 to 11 halogen atoms which may be the same or different.

A specific preferred example of the additional substituent is one, more groups selected from the group consisting of:

a fluorine atom, a chlorine atom, a bromine atom, cyano, nitro, amino, formyl, carbamoyl, thiocarbamoyl, methyl, ethyl, n-propyl, isopropyl, n-butyl, isobutyl, sec-butyl, t-butyl, methoxy, ethoxy, n-propoxy, isopropoxy, methylthio, ethylthio, n-propylthio, isopropylthio, methylsulfinyl, methylsulfonyl, ethylsulfinyl, ethylsulfonyl, trifluoromethyl, trifluoroethyl, trifluoromethoxy, difluoromethoxy, difluorochloromethoxy, trifluoroethoxy, difluoromethylthio, chlorodifluoromethylthio, trifluoromethylthio, trifluoromethylsulfinyl, trifluoromethylsulfonyl, acetylamino, formylamino, N-formyl-N-methylamino, methylamino, ethylamino, n-propylamino, isopropylamino, dimethylamino, diethylamino, acetyl, propionyl, acetoxy, methoxycarbonyl, ethoxycarbonyl, methylsulfonyloxy, ethylsulfonyloxy, methoxyiminomethyl, ethoxyiminomethyl, methoxyiminoethyl and ethoxyiminoethyl;

trimethylene, tetramethylene, methylenedioxy, ethylenedioxy and 1,4,7,10,13-pentoxatridecamethylene, wherein these groups may be substituted by one or two or more substituents selected from the group consisting of a fluorine atom, a chlorine atom, methyl, trifluoromethyl, ethyl, n-propyl and i-propyl, and are present as a chain which is substituted in its both ends at adjacent positions on the ring to form a ring; and cyclopropyl, cyclobutyl, cyclopentyl, cyclohexyl, phenyl, wherein these groups may be substituted by one, two or more substituents selected from the group consisting of a fluorine atom, a chlorine atom, methyl, trifluoromethyl, ethyl, n-propyl, isopropyl, n-butyl, sec-butyl, isobutyl and t-butyl.

A specific example of more preferred groups represented by $R_3$ is selected from the group consisting of:

a hydrogen atom, 4-phenoxyphenyl, 4-(4'-t-butylphenoxy)phenyl, 4-(3'-trifluoromethylphenoxy)phenyl, 3-phenoxyphenyl, 2-phenoxyphenyl, 4-benzylphenyl, 4-(4'-methoxyphenoxy)phenyl, 3-trifluoromethyl-4-(4'-trifluoromethylphenoxy)phenyl or 4-(4'-phenylphenoxy)phenyl;

4-(4'-methylphenoxy)phenyl or 4-(4'-methylphenoxy)phenyl;

4-(4'-methylphenoxy)-3-trifluoromethylphenyl, 3-chloro-4-phenoxyphenyl, 4-phenoxy-3-trifluoromethylphenyl, 3-methyl-4-phenoxyphenyl, or 3-methoxy-4-(4'-methylphenoxy)phenyl;

4-(2',4'-di-t-butylphenoxy)phenyl, 4-(3',5'-di-t-butylphenoxy)phenyl, 3-chloro-4-(4'-chlorophenoxy)phenyl, 3-methyl-4-(4'-methoxyphenoxy)phenyl, 1-(1-naphthyl)ethyl, 3-chloro-4-(4'-methoxyphenoxy)phenyl, 3-chloro-4-(4'-methylphenoxy)phenyl, 3-methyl-4-(4'-methylphenoxy)phenyl, 4-(4'-trifluoromethoxyphenoxy)phenyl or 4-(3'-trifluoromethoxyphenoxy)phenyl;

3-methyl-4-(4'-trifluoromethylphenoxy)phenyl, 4-(4'-methylphenoxy)-2-trifluoromethylphenyl, 2,4-di-(4'-methylphenoxy)phenyl, 4-benzyloxyphenyl, 3-benzyloxyphenyl, cyclododecyl, cyclooctyl, 1-adamantyl, 1-adamantanemethyl, 4-cyclohexylphenyl, 3,4-ethylenedioxyphenyl, 4-(4'-nitrophenoxy)phenyl, 2,6-dimethyl-4-phenoxyphenyl, 4-(4'-N-isopropylaminophenoxy)phenyl, 4-(4'-isobutyrylpiperazin-1'-yl)phenyl, 2-methylcyclohexyl, cyclopropyl, cyclopentyl, cyclobutyl, 4-(2'-phenoxyethyloxy)phenyl, 4-(3'-phenoxypropyloxy)phenyl, 4-(3'-phenylpropyloxy)phenyl, 2-pyridyl, 3-pyridyl, 4-pyridyl, phenyl, 4-methylphenyl, 4-chlorophenyl, 4-fluorophenyl, 4-t-butylphenyl, 4-neopentylphenyl, 2-fluoro-4-methylphenyl, 3,4-dichlorophenyl, 3,5-difluorophenyl, 3,5-di-t-butylphenyl, 4-trifluoromethylphenyl, 4-trifluoromethoxyphenyl, 2-phenylcyclopropyl, cyclohexyl, 1-cyclohexenyl, 4-phenetyloxyphenyl, 3-chloro-4-phenetyloxyphenyl, 4-(4'-chlorophenetyloxy)phenyl, 4-methylcyclohexyl, cycloheptyl, cyclooctyl, 3-methyl-4-(3'-trifluoromethylphenoxy)phenyl, 4-t-butyl-2-chlorophenyl, 4-t-butyl-2,6-dimethylphenyl, 5-t-butylisoxazol-3-yl, or 4-t-butylthiazol-2-yl;

4-phenylthiophenyl, 2-methoxy-4-phenoxyphenyl, 3-(3-pyridyl)phenyl, 4-phenylaminophenyl or 4-(4-morpholinyl)phenyl; and 1-benzylpiperidin-4-yl, 4-(4'-aminophenoxy)phenyl, 4-benzoylphenyl, 1-indanyl, 1,2,3,4-tetrahydronaphtho-1-yl, 1-homopiperidinyl, 2-hydroxycyclohexyl or 4-hydroxycyclohexyl.

Particularly preferred picolinamide derivatives represented by formula (1) according to the present invention are such that, in formula (1), A represents a bond, methylene chain, 1,1- or 1,2-ethylene chain, 1,2-, 1,3- or 2,2-propylene chain, 1,4-butylene chain, 2,4-butylene chain, 3,3-dimethyl-1,4-butylene chain, 1,1,3,3-tetramethyl-1,4-butylene chain, 1,5-pentyl chain, 2,5-dichloro-1,5-pentyl chain, hexamethylene chain, heptamethylene chain or octamethylene chain;

$R_1$ represents 4-methoxy, 6-methoxy, 4,5-dimethoxy or 4,6-dimethoxy;

$R_2$ represents a hydrogen atom, benzyl, acetyl or propionyl; and $R_3$ represents a hydrogen atom, 4-phenoxyphenyl, 4-(4'-t-butylphenoxy)phenyl, 4-(3'-trifluoromethylphenoxy)phenyl, 3-phenoxyphenyl, 2-phenoxyphenyl, 4-benzylphenyl, 4-(4'-methoxyphenoxy)phenyl, 3-trifluoromethyl-4-(4'-trifluoromethylphenoxy)phenyl or 4-(4'-phenylphenoxy)phenyl, 4-(4'-methylphenoxy)phenyl or 4-(4'-methylphenoxy)phenyl, 4-(4'-methylphenoxy)-3-trifluoromethylphenyl, 3-chloro-4-phenoxyphenyl, 4-phenoxy-3-trifluoromethylphenyl, 3-methyl-4-phenoxyphenyl, or 3-methoxy-4-(4'-methylphenoxy)phenyl, 4-(2',4'-di-t-butylphenoxy)phenyl, 4-(3',5'-di-t-butylphenoxy)phenyl, 3-chloro-4-(4'-chlorophenoxy)phenyl, 3-methyl-4-(4'-methoxyphenoxy)phenyl, 1-(1-naphthyl)ethyl, 3-chloro-4-(4'-methoxyphenoxy)phenyl, 3-chloro-4-(4'-methylphenoxy)phenyl, 3-methyl-4-(4'-methylphenoxy)phenyl, 4-(4'-trifluoromethoxyphenoxy)phenyl or 4-(3'-trifluoromethoxyphenoxy)phenyl, 3-methyl-4-(4'-trifluoromethylphenoxy)phenyl, 4-(4'-methylphenoxy)-2-trifluoromethylphenyl, 2,4-di-(4'-methylphenoxy)phenyl, 4-benzyloxyphenyl, 3-benzyloxyphenyl, cyclododecyl, cyclooctyl, 1-adamantyl, 1-adamantanemethyl, 4-cyclohexylphenyl, 3,4-ethylenedioxyphenyl, 4-(4'-nitrophenoxy)phenyl, 2,6-dimethyl-4-phenoxyphenyl, 4-(4'-N-isopropylaminophenoxy)phenyl, 4-(4'-isobutyrylpiperazin-1'-yl)phenyl, 2-methylcyclohexyl, cyclopropyl, cyclopentyl, cyclobutyl, 4-(2'-phenoxyethyloxy)phenyl, 4-(3'-phenoxypropyloxy)phenyl, 4-(3'-phenylpropyloxy)phenyl, 2-pyridyl, 3-pyridyl, 4-pyridyl, phenyl, 4-methylphenyl, 4-chlorophenyl, 4-fluorophenyl, 4-t-butylphenyl, 4-neopentylphenyl, 2-fluoro-4-methylphenyl, 3,4-dichlorophenyl, 3,5-difluorophenyl, 3,5-di-t-butylphenyl, 4-trifluoromethylphenyl, 4-trifluoromethoxyphenyl, 2-phenylcyclopropyl, cyclohexyl, 1-cyclohexenyl, 4-phenetyloxyphenyl, 3-chloro-4-phenetyloxyphenyl, 4-(4'-chlorophenetyloxy)phenyl, 4-methylcyclohexyl, cycloheptyl, cyclooctyl, 3-methyl-4-(3'-trifluoromethylphenoxy)phenyl, 4-t-butyl-2-chlorophenyl, 4-t-butyl-2,6-dimethylphenyl, 5-t-butylisoxazol-3-yl, or 4-t-butylthiazol-2-yl, 4-phenylthiophenyl, 2-methoxy-4-phenoxyphenyl, 3-(3-pyridyl)phenyl, 4-phenylaminophenyl, or 4-(4-morpholinyl)phenyl or 1-benzylpiperidin-4-yl, 4-(4'-aminophenoxy)phenyl, 4-benzoylphenyl, 1-indanyl, 1,2,3,4-tetrahydronaphtho-1-yl, 1-homopiperidinyl or 2-hydroxycyclohexyl.

These picolinamide derivatives have particularly high activity against harmful organisms, and, at the same time, have high safety against plants.

According to another embodiment of the present invention, the compounds represented by formula (1) may exist as a salt.

Examples of salts usable herein include pharmaceutically acceptable salts. Specific examples thereof include lithium salts, sodium salts, potassium salts, magnesium salts, calcium salts, and salts with ammonia and proper nontoxic amines, for example, $C_1$–$C_6$ alkylamine (for example, triethylamine) salts, $C_1$–$C_6$ alkanolamine (for example, diethanolamine or triethanolamine) salts, procaine salts, cyclohexylamine (for example, dicyclohexylamine) salts, benzylamine (for example, N-methylbenzylamine, N-ethylbenzylamine, N-benzyl-β-phenetylamine, N,N-dibenzylethylenediamine, or dibenzylamine) salts, and heterocyclic amine (for example, morpholine or N-ethylpyridine) salts or inorganic acid salts, for example, hydrohalides, such as hydrofluorides, hydrochlorides, hydrobromides, and hydroiodides, sulfates, nitrates, phosphates, perchlorates and carbonates, and organic acid salts, for example, salts of carboxylic acids, such as acetic acid, trichloroacetic acid, trifluoroacetic acid, hydroxyacetic acid, lactic acid, citric acid, tartaric acid, oxalic acid, benzoic acid, mandelic acid, butylic acid, maleic acid, propionic acid, formic acid, and malic acid, salts of amino acids, such as alginic acid, aspartic acid, and glutamic acid, and other organic acid salts, such as salts of methanesulfonic acid and p-toluenesulfonic acid.

Production of Picolinamide Derivative Represented by Formula (1)

The picolinamide derivatives of formula (1) may be produced by chemically reacting various starting compounds. Therefore, according to another aspect of the present invention, there is provided a process for producing a picolinamide derivative of formula (1) or a salt thereof.

The production process of a picolinamide derivative of formula (1) according to the present invention will be described in detail. However, it should be noted that the scope of the present invention is not limited by the following production process. The compound of formula (1) according to the present invention may be produced, for example, through a scheme 1 below, although the present invention is not limited to this scheme only.

Scheme 1

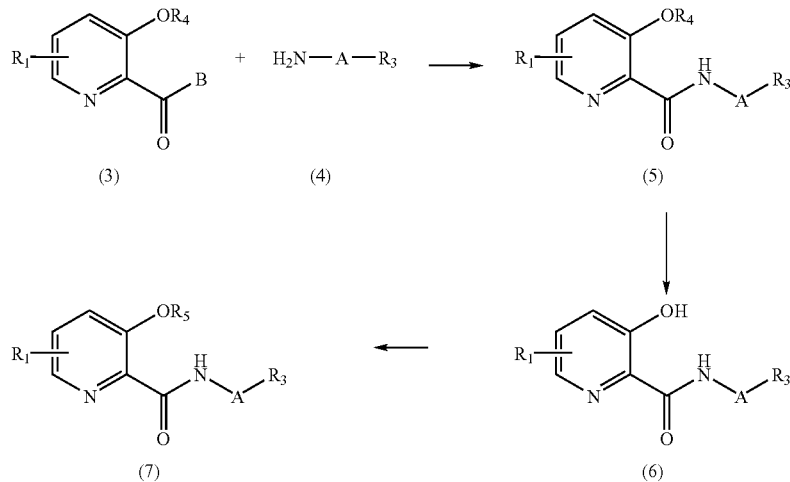

The compounds in scheme 1, A, $R_1$, and $R_3$ are as defined above in connection with formula (1), and B and $R_4$ are as defined above in connection with formula (2). $R_5$ represents lower acyl, such as acetyl, propionyl or pivaloyl. The compounds of formulae (5), (6), and (7) are picolinamide derivatives of formula (1) according to the present invention.

According to this process, the picolinic acid derivative of formula (3) is reacted with an amine compound of formula (4) in the presence of a suitable condensation agent or an acid linking agent, or under aminolysis reaction conditions, in an inert solvent. Thereafter, when $R_4$ is a group other than a hydrogen atom, if necessary, the removal of $R_4$ and then optionally acylation are carried out to give picolinamide derivatives of formulae (5), (6) and (7).

Condensation agents usable, in the case where B in formula (3) represents hydroxyl, include: acid halide formers, such as phosphorus trichloride, phosphorus tribromide, phosphorus pentachloride, phsophorus oxychloride, and thionyl chloride; mixed acid anhydrides or acid halide of ethyl chloroformate and methanesulfonyl chloride; carbodiimides, such as N,N'-dicyclohexylcarbodiimide (DCC), 1-ethyl-3-(3-dimethylaminopropyl)carbodiimide hydrochloride (WSCI.HCl); and other condensation agents, for example, N,N-carbonyldiimidazole, 2-ethoxy-N-ethoxycarbonyl-1,2-dihydroquinoline (EEDQ) and triphenylphosphine-carbon tetrachloride (complex).

Alternatively, the picolinamide derivative may be produced by condensing 1-hydroxybenzotriazole or N-hydroxysuccinimid and a picolinic acid derivative with N,N'-dicyclohexylcarbodiimide to give an active ester compound which is then reacted with an amine compound.

When acid salts of a picolinic acid derivative and an amine compound are used addition of a base, such as triethylamine, can offer a smooth reaction.

Solvents usable herein include: aromatic hydrocarbons, such as benzene, toluene and xylene; halogenated aromatic hydrocarbons, such as chlorobenzene and dichlorobenzene; aliphatic hydrocarbons, such as hexane, cyclohexane and petroleum ether; aliphatic halogenated hydrocarbons, such as dichloromethane, 1,2-chloroethane, chloroform and carbon tetrachloride; ethers, such as diethyl ether, diisopropyl ether, dioxane, tetrahydrofuran, ethylene glycol dimethyl ether and ethylene glycol diethyl ether; ketones, such as acetone, 2-butanone and methyl isobutyl ketone; nitrites, such as acetonitrile, propionitrile and benzonitrile; amides, such as N,N-dimethylformamide and hexamethylphosphoric triamide (HMPA); sulfoxides, such as dimethylsulfoxide; or mixtures thereof.

The amount of reagents used in the reaction is not particularly limited. Preferably, however, based on one mol of the picolinic acid derivative represented by formula (3), in general, the amine compound of formula (4) is used in an amount of 1.0 to 2.0 mol, preferably 1.0 to 1.3 mol, and the condensation agent is used in an amount of 1.0 to 5.0 mol, preferably 1.0 to 2.5 mol. The reaction temperature is not particularly limited. In general, however, the reaction temperature is in the range of −10° C. to the boiling temperature of the solvent used. The reaction time may vary depending upon concentration and temperature. In general, a reaction for 5 to 10 hr suffices for the production.

Regarding the base added in the case where the acid addition salt of a picolinic acid derivative and an acid addition salt of an amine compound are used, a base may be used in an amount of 1.0 to 2.0 mol, preferably 1.0 to 1.3 mol, based on one mol of the acid addition salt of the picolinic acid derivative, and may be used in an amount of 1.0 to 2.0 mol, preferably 1.0 to 1.3 mol, based on one mol of the acid addition salt of the amine compound.

Solvents usable, in the case where B in formula (3) represents a halogen atom, may be those described above. The acid linking agents usable herein include: alkali metal hydroxides or alkaline earth metal hydroxides, such as sodium hydroxide, potassium hydroxide, and calcium hydroxide; ammonium hydroxide; carbonates of alkali metals, such as sodium carbonate, potassium carbonate, sodium hydrogencarboante and potassium hydrogencarbonate; ammonium carbonate; acetates of alkali metals or alkaline earth metals, such as sodium acetate, potassium acetate and calcium acetate; ammonium acetate; hydrides of alkali metals or alkaline earth metals, such as sodium hydride, potassium hydride, and calcium hydride; and tertiary amines, such as trimethylamine, triethylamine, N,N-dimethylaniline, pyridine, 4-(dimethylamino)pyridine, diazabicyclooctane (DABCO), diazabicyclononene (DBN) and diazabicycloundecene (DBU).

The amount of the reagents used in the reaction is not particularly limited. Preferably, however, based on one mol of the acid halide of the 3-hydroxypicolinic acid derivative, in general, the amine compound of formula (4) is used in an amount of 1.0 to 2.0 mol, preferably 1.0 to 1.3 mol, and the acid linking agent is used in an amount of 1.0 to 5.0 mol, preferably 1.0 to 2.5 mol. The reaction temperature is not particularly limited. In general, however, the reaction temperature is in the range of $-10°$ C. to the boiling temperature of the solvent used. The reaction time may vary depending upon the concentration and temperature. In general, a reaction for 1 to 5 hr suffices for the production.

Solvents usable, in the case where B in formula (3) represents alkoxy, may be those described above. The reaction may be carried out under conventional aminolysis conditions.

The amount of the reagents used in the reaction is not particularly limited. Preferably, however, based on one mol of the alkoxy form of the 3-hydroxypicolinic acid derivative, in general, the amine compound of formula (4) is used in an amount of 1.0 to 10.0 mol, preferably 1.0 to 3.0 mol. The reaction temperature is not particularly limited. In general, however, the reaction temperature is in the range of $-10°$ C. to the boiling temperature of the solvent used. If necessary, the reaction is allowed to proceed under a pressure of 2 to 15 kbar. The reaction time may vary depending upon the concentration and temperature. In general, a reaction for 1 to 12 hr suffices for the production.

If necessary, the picolinamide derivatives of formula (5) thus obtained, when $R_4$ represents a group other than a hydrogen atom, can be easily lead to a 3-hydroxy compound of formula (6) or an acid addition salt thereof by conventional methods.

Methods usable herein are as follows. When $R_4$ represents optionally substituted benzyl, catalytic hydrogenation or acid hydrolysis is suitable. On the other hand, when $R_4$ represents methoxymethyl or methoxyethoxymethyl, acid hydrolysis is suitable. The 3-hydroxy compound thus obtained can be easily acylated by a conventional method to give a 3-acyloxy compound represented by formula (7). Solvents and acid linking agents usable herein may be those described above in connection with scheme 1. Acylation agents include acetic anhydride, propionic anhydride, acetyl chloride, acetyl bromide, propionyl chloride and pivaloyl chloride.

The reaction mixture containing the picolinamide derivative compound of formula (1) according to the present invention may be purified by extraction, concentration, filtration, chromatography, recrystallization and other conventional means.

Use of Picolinamide Derivative of Formula (1)/Harmful Organism Control Composition One aspect of the present invention is based on properties such that the picolinamide derivatives of formula (1) have potent activity against harmful organisms and, at the same time, do not have phytotoxicity against agricultural and gardening plants, as objects to which the compounds of the present invention are applied for preventive and exterminating purposes, and human beings and beasts.

Specifically, the picolinamide derivatives of formula (1) have potent activity against harmful organisms, and are useful as an active component of control agents for agriculture and gardening, for preventing or exterminating organisms harmful to the agricultural production, particularly plant pathogenic fungi, pest insects, weeds or beasts.

The picolinamide derivatives of formula (1) according to the present invention have potent activity and excellent preventive or therapeutic effect against various plant diseases. In particular, the picolinic acid derivatives of formula (1) may be used for treating plant pathogenic fungi infectious diseases caused by pathogenic fungi sensitive to the derivatives of formula (1).

The plant pathogenic fungi control agent comprising as an active component the picolinamide derivative of formula (1) according to the present invention is preferably supplied as a proper dosage form, according to various dosage forms, by using a carrier and optionally blending proper adjuvants.

For example, the picolinamide derivative of formula (1) may be mixed, for example, with a solid carrier, a liquid carrier, a gaseous carrier, and a bait, and, if necessary, a surfactant and other additives for preparations are added thereto to formulate the control agent into oil solutions, emulsifiable concentrates, wettable powder, floables, granules, dust, aerosols and sprays.

Solid carrier usable in the formulation include, for example, fine powders or particulates of clays (for example, kaolin clay, diatomaceous earth, synthetic hydrous silicon oxide, bentonite, fubasami clay, acid clay), talcs, ceramics and other inorganic minerals (for example, celite, quartz, sulfur, activated carbon, calcium carbonate and hydrous silica), chemical fertilizers (for example, ammonium sulfate, ammonium phosphate, ammonium nitrate, urea and ammonium chloride). Liquid carriers include, for example, water, alcohols (for example, methanol and ethanol), ketones (for example, acetone and methyl ethyl ketone), aromatic hydrocarbons (for example, benzene, toluene, xylene, ethylbenzene and methylnaphthalene), aliphatic hydrocarbons (for example, hexane, cyclohexane, kerosene and gas oil), esters (for example, ethyl acetate and butyl acetate), nitriles (for example, acetonitrile and isobutyronitrile), ethers (for example, diisopropyl ether and dioxane), acid amides (for example, N,N-dimethylformamide and N,N-dimethylacetamide), halogenated hydrocarbons (for example, dichloromethane, trichloroethane and carbon tetrachloride), dimethyl sulfoxide and vegetable oils (for example, soybean oil and cotton seed oil). Gaseous carriers, that is, propellants, include, for example, butane gas, LPG (liquefied petroleum gas), dimethyl ether and carbon dioxide.

Additives preparations include, for example, fixing agents or dispersants, such as casein, gelatin, polysaccharides (for example, starch powder, gum arabic, cellulose derivatives and arginic acid), lignin derivatives, bentonite, saccharides, synthetic water-soluble polymers (for example, polyvinyl alcohol, polyvinylpyrrolidone, and polyacrylic acids), for example, PAP (for example, acidic isopropyl phosphate), BHT (for example, 2,6-di-tert-butyl-4-methylphenol), BHA (for example, a mixture of 2-tert-butyl-4-methoxyphenol with 3-tert-butyl-4-methoxyphenol), vegetable oils, mineral oils, surfactants, stabilizers such as fatty acids (for example, stearic acid), their esters or salts.

Surfactants include, for example, alkylsulfonic esters, alkylsulfonic acid salts, alkylarylsulfonic acid salts, alkyl aryl ethers, and polyoxyethylenation products thereof, polyethylene glycol ethers, polyhydric alcohol esters and sugar alcohol derivatives.

In the plant pathogenic fungi control agent according to the present invention, preferably, the picolinamide derivative of formula (1) is generally contained in an amount of about 0.01 to 99.5% by weight, preferably about 0.05 to 90% by weight; in the case of oils, is contained in an amount of about 0.1 to 20% by weight, preferably about 0.5 to 5% by weight; in the case of emulsifiable concentrates, is contained in an amount of about 1 to 90% by weight, preferably about 5 to 50% by weight; in the case of wettable powders and floables, is contained in an amount of about 1 to 90% by weight, preferably about 10 to 80% by weight; in the case of granules, is contained in an amount of about 0.1 to 50% by weight, preferably about 0.5 to 25% by weight; in the case of dust, is contained in an amount of about 0.1 to 40% by weight, preferably about 0.3 to 25% by weight; and in the case of aerosols, is contained in an amount of about 0.05 to 10% by weight, preferably about 0.1 to 5% by weight.

In use, the plant pathogenic fungi control agent according to the present invention may be used either as such or after dilution with water. Alternatively, the plant pathogenic fungi control agent according to the present invention may be used in combination with or as a mixture with other bactericides, nematicides, miticides, herbicides, growth-regulating substances of plants, or synergists.

The application rate and application concentration in the control of plant pathogenic fungi according to the present invention may vary depending upon type, application season, application sites, application methods, type of diseases, and level of damage. Specifically, the application rate is generally about 0.1 to 1000 g per 10 ares, preferably about 1 to 100 g per 10 ares, in terms of the active component. When the emulsifiable concentrate, the wettable powder, or the floables is used after dilution with water, the application concentration is generally about 0.1 to 10000 ppm, preferably about 10 to 1000 ppm, and the granules and the dust are preferably applied as such without dilution.

The plant pathogenic fungi control agent according to the present invention may be applied to agricultural and garden plants, as well as to environment under which the plant pathogenic fungi grow (for example, fields and beds), and equipment for agricultural and gardening applications (for example, tractors and combines).

The plant pathogenic fungi control agent according to the present invention is useful for various diseases harmful to agriculture and gardening, for examples, various diseases of vegetables, fruit trees, paddy rice, or garden plants, and is very useful for plant diseases caused by representative plant pathogenic fungi belonging to deuteromyces, ascomycotina, and basidiomycetes. In particular, the plant pathogenic fungi control agent according to the present invention has significant control effect against plant diseases, such as rice blast, cucumber anthracnose, powdery mildew of cucumber, and wheat leaf rust.

Picolinic Acid Derivative of Formula (2)

In formula (2), B represents hydroxyl, a halogen atom, or alkoxy having 1 to 6 carbon atoms; $R_1$ represents one, two or more groups, which may be the same or different, selected from the group consisting of alkoxy having 1 to 4 carbon atoms and haloalkoxy having 1 to 4 carbon atoms; and $R_4$ represents a hydrogen atom, benzyl, alkyl having 1 to 4 carbon atoms or alkanoyl having 1 to 4 carbon atoms, in which the groups other than the hydrogen atom may be substituted. In this case, the compounds of formula (2), wherein $R_1$ represents 4-methoxy with $R_4$ representing hydrogen or benzyl, are excluded from the scope of the present invention.

Specific examples of preferred B include hydroxyl, a chlorine atom, a bromine atom, methoxy, ethoxy, methoxymethoxy, benzyloxy, and 4-methoxybenzyloxy.

Specific examples of preferred $R_1$ include methoxy, ethoxy, 1-propyloxy, isopropoxy, 1-butyloxy, 2-butyloxy, t-butyloxy, trifluoromethoxy, difluoromethoxy, fluoromethoxy, difluorochloromethoxy or trifluoroethoxy, dimethoxy, and diethoxy. Examples of more preferred $R_1$ include methoxy, ethoxy, trifluoromethoxy, difluoromethoxy, fluoromethoxy and difluorochloromethoxy.

Specific examples of preferred $R_4$ include a hydrogen atom, benzyl, p-nitrobenzyl, p-methoxybenzyl, methoxymethyl, methoxyethoxymethyl and diphenylmethyl.

According to another embodiment of the present invention, the picolinic acid derivative of formula (2) may exist as a salt.

Examples of salts usable herein include pharmaceutically acceptable salts. Specific examples thereof include lithium salts, sodium salts, potassium salts, magnesium salts, calcium salts, and salts with ammonia and proper nontoxic amines, for example, $C_1$–$C_6$ alkylamine (for example, triethylamine) salts, $C_1$–$C_6$ alkanolamine (for example, diethanolamine or triethanolamine) salts, procaine salts, cyclohexylamine (for example, dicyclohexylamine) salts, benzylamine (for example, N-methylbenzylamine, N-ethylbenzylamine, N-benzyl-β-phenetylamine, N,N-dibenzylethylenediamine or dibenzylamine) salts and heterocyclic amine (for example, morpholine or N-ethylpyridine) salts, or inorganic acid salts, for example, hydrohalides, such as hydrofluorides, hydrochlorides, hydrobromides, and hydroiodides, sulfates, nitrates, phosphates, perchlorates and carbonates, and organic acid salts, for example, salts of carboxylic acids, such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, and malic acid, salts of amino acids, such as alginic acid, aspartic acid, and glutamic acid, and other organic acid salts such as salts of methanesulfonic acid and p-toluenesulfonic acid.

The picolinic acid derivatives of formula (2) and salts thereof are useful because they can be used as a starting compound for picolinamide derivatives of formula (1).

Production Process of Picolinic Acid Derivative Represented by Formula (2)

The picolinic acid derivative of formula (2) according to the present invention may be specifically produced by processes shown in the following schemes 2-1, 2-2 and 2-3. However, it should be noted that the scope of the present invention is not limited by these processes.

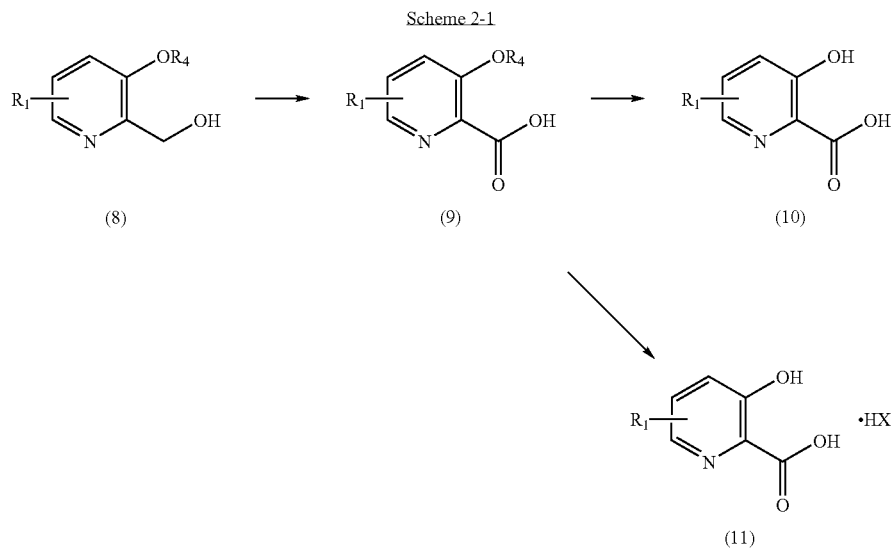

In each picolinic acid derivative in scheme 2-1, $R_1$ represents one or more same or different alkoxys having 1 to 4 carbon atoms or haloalkoxys having 1 to 4 carbon atoms; $R_4$ represents a hydrogen atom, an optionally substituted benzyl, an optionally substituted alkyl having 1 to 4 carbon atoms or alkanoyl having 1 to 4 carbon atoms; and X represents a halogen atom, preferably a chlorine, bromine or iodine atom.

According to the process shown in scheme 2-1, a substituted 3-benzyloxy-2-hydroxymethylpyridine represented by formula (8), disclosed in EP 0208452 and EP 0304732, is oxidized in an inert solvent to give a substituted 3-benzyloxypicolinic acid represented by formula (9). Inert solvents include, for example, water. Oxidizing agents usable herein include, for example, potassium permanganate and sodium bichromate. The reaction temperature may vary depending upon the type of the reaction and the reagent and solvent used. In general, however, the reaction is carried out at about—20° C. to 100° C., preferably about 50 to 100° C. The reaction satisfactorily proceeds at a temperature of about 50 to 100° C. to give the title compound in high yield. Next, catalytic hydrogenation or acid hydrolysis is carried out to give a substituted 3-hydroxypicolinic acid of formula (10) or an acid addition salt thereof of formula (11). The catalytic hydrogenation or the acid hydrolysis can be easily carried out by a conventional method.

Alternatively, 6-substituted 3-hydroxypicolinic acid or an acid addition salt thereof may be produced according to scheme 2-2.

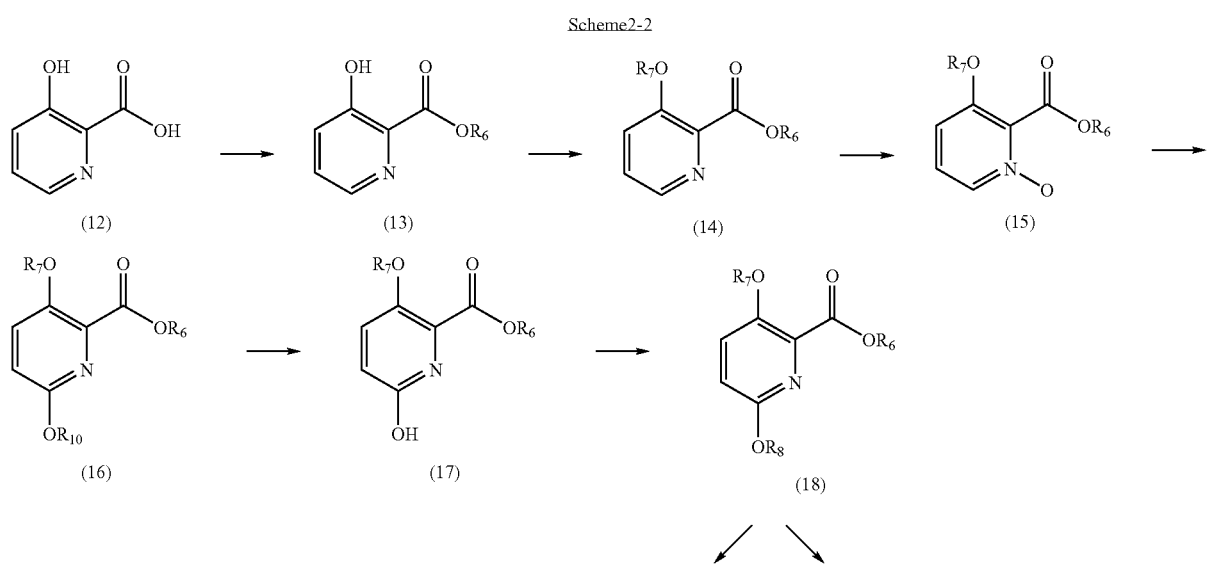

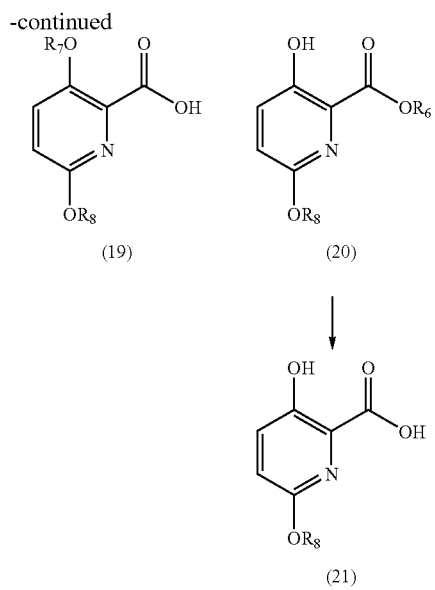

In each compound shown in scheme 2-2, $R_6$ represents alkyl having 1 to 8 carbon atoms; $R_7$ represents an optionally substituted benzyl or optionally substituted alkyl having 1 to 4 carbon atoms; $R_8$ represents alkoxy having 1 to 4 carbon atoms or haloalkoxy having 1 to 4 carbon atoms; and $R_{10}$ represents formyl, acetyl, trichloroacetyl, trifluoroacetyl, chloroacetyl, propionyl, butyryl, isobutyryl, pivaloyl or phenoxyacetyl.

Specifically, a 3-hydroxypicolinic acid represented by formula (12) (a commercially available product may be used) is subjected to lower alkylation by a conventional esterification method. More specifically, the 3-hydroxypicolinic acid represented by formula (12) is treated with a corresponding lower alcohol in the presence of an acid catalyst, or alternatively is treated with a lower alkyl halide in the presence of a base in an inert solvent to give a 3-hydroxypicolinic ester of formula (13) in high yield. Here lower alkyl refers to alkyl having 1 to 8 carbon atoms, and suitable examples thereof include methyl, ethyl, n-propyl, isopropyl, n-butyl, and t-butyl. Acids usable as the acid catalyst include, for example, hydrogen chloride, sulfuric acid, and p-toluenesulfonic acid. The inert solvent is not particularly limited, and examples thereof include N,N-dimethylformamide, dimethylsulfoxide, acetonitrile, dioxane and tetrahydrofuran. Bases include: organic amines, such as triethylamine and pyridine; and inorganic bases, such as sodium carbonate and potassium carbonate. Lower alkyl halides include methyl iodide, ethyl iodide, ethyl bromide, 1-bromopropane, and 1-bromobutane. Alternatively, a simpler method may be used. Specifically, the 3-hydroxypicolinic acid represented by formula (12) may be treated with diazomethane or trimethylsilyldiazomethane in an inert solvent to give a methyl ester or may be treated with isobutene in the presence of an acid catalyst to give a t-butyl ester. The temperature used in these esterification reactions may vary depending upon the type of the reaction and the reagent and the solvent used. In general, however, the reaction temperature is about –20° C. to 100° C., preferably about 0 to 25° C. The reaction satisfactorily proceeds at this temperature to give the title compound in high yield.

Next, a protective group is introduced into hydroxyl at the 3-position. The protective group is preferably removable under reduction conditions or acidic conditions. Examples of suitable protective groups include benzyl, p-methoxybenzyl, p-nitrobenzyl, methoxymethyl, methoxyethoxymethyl and diphenylmethyl.

The compound (13) can be easily reacted with a corresponding halogenation reagent in an inert solvent in the presence of a base to convert the compound (13) to the compound of formula (14). In the case of diphenylmethyl, the treatment with diphenyldiazomethane in an inert solvent is an optimal method. Examples of inert solvents include N,N-dimethylformamide, dimethylsulfoxide, acetonitrile, dioxane, tetrahydrofuran and acetone. Bases include sodium hydride and potassium carbonate. The halogen atom in the halogenation agent refers to chorine, bromine or iodine. The reaction temperature is generally about 0 to 80° C., preferably about 25 to 50° C.

The compound (14) can be easily converted, by a conventional method involving the oxidation of nitrogen located within the pyridine ring, to an N-oxide compound of formula (15). The N-oxide compound of formula (15), when heated together with an acylation agent, is once converted to an N-acyloxy compound, and then causes a conventional thermal rearrangement reaction to give a 6-acyloxy compound of formula (16). Specific examples of suitable acyls include acyls having a small number of carbon atoms, such as formyl, acetyl, trichloroacetyl, trifluoroacetyl, propionyl, butyryl and isobutyryl. Among them, acetyl is most preferred. Acylating agents include corresponding carboxylic anhydride or acid chloride, and, in the case of acetylation, acetic anhydride is most preferred. Suitable reaction conditions are such that the reaction system is heated in the absence of a solvent or in the presence of an inert solvent (an inert solvent having a relatively high boiling point, such as toluene or xylene, being suitable) at 90 to 130° C. The 6-acyloxy compound of formula (16) may be deacylated under conventional basic conditions to give a 6-hydroxy compound of formula (17).

Next, hydroxyl located at the 6-position of the 6-hydroxy compound of formula (17) is alkylated or haloalkylated to give a 6-alkoxy or 6-haloalkoxy compound of formula (18). In the case of methylation, diazomethane or trimethylsilyldiazomethane, which enables methylation under mild conditions, is suitable as an alkylation agent. In a general method, an alkylation agent, such as methyl iodide, dimethyl sulfate, methyl p-toluenesulfonate, ethyl bromide, diethyl sulfate, 1-bromopropane, 1-bromobutane, or 1-bromopentane, or a haloalkylation agent, such as chloroiodomethane or iodotrifluoromethane, is used in an inert solvent (for example, N,N-dimethylformamide, dimethylsulfoxide, or acetone) in the presence of a base (for example, sodium hydride, t-butoxypotassium or potassium carbonate). The reaction temperature is in the range of about 0 to 80° C., preferably in the range of about 25 to 60° C.

Finally, the removal of the protective group for hydroxyl at the 3-position and the deesterification of the carobxyl at the 2-positon can be easily carried out by conventional methods. Thus, a deesterification product of formula (19), a compound of formula (20) wherein the protective group at the 3-positon has been removed, and a 3-hydroxy-6-substituted picolinic acid of formula (21) or an acid salt thereof can be obtained. 4,6-Disubstituted 3-hydroxypicolinic acid, 4,5-disubstituted 3-hydroxypicolinic acid, or an acid salt thereof may also be produced according to scheme 2-3.

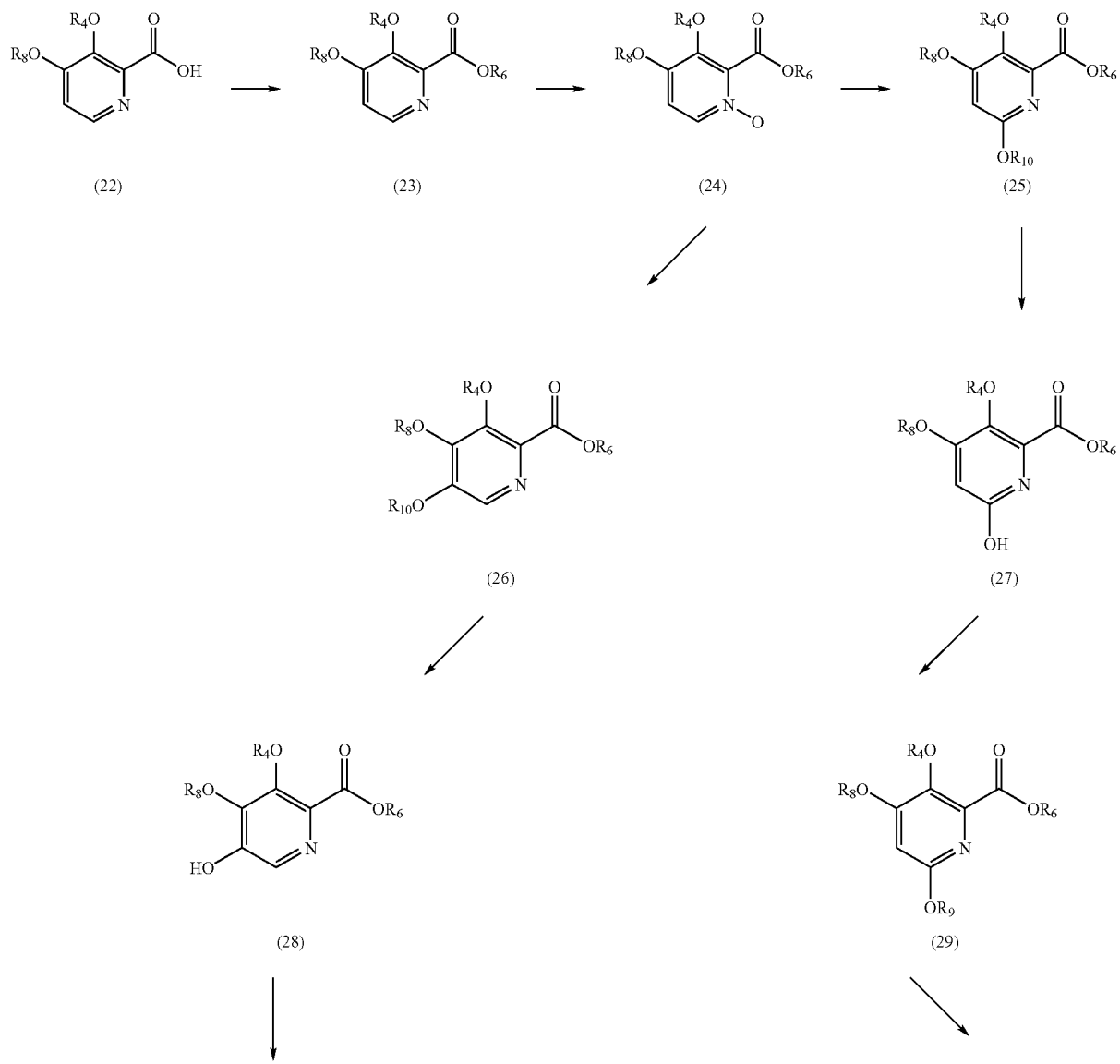

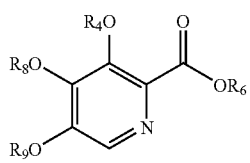

(30)

-continued

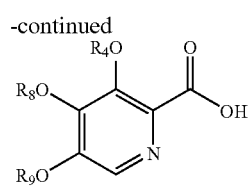

(32)

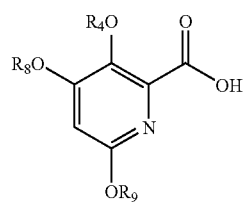

(31)

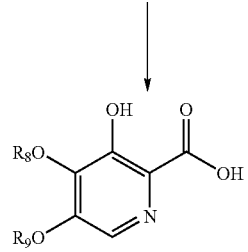

(34)

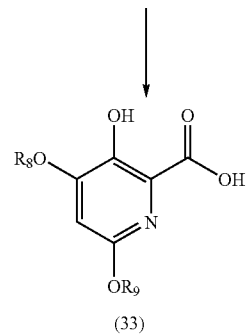

(33)

In the compounds in scheme 2-3, the substituents $R_4$, $R_6$, $R_8$ and $R_{10}$ are as defined above; and $R_9$ represents alkoxy having 1 to 4 carbon atoms or haloalkoxy having 1 to 4 carbon atoms.

Parts of the products in step 2-1, compound of formula (22) are provided as a starting compounds, and are esterified and oxidized in the similar manner as used in connection with 3-hydroxy-6-substituted picolinic acid to give a picolinic ester of formula (23) which is then converted to an N-oxide compound of formula (24). The acylation is then carried out in the similar manner as in the case of 3-hydroxy-6-substituted picolinic acid, and is subjected to a rearrangement reaction. In this case, both compounds of formula (25), wherein acyloxy has been rearranged to the 6-positoin, and a compound of formula (26), wherein acyloxy has been rearranged to the 5-position, are produced. These compounds can be easily separated by silica gel chromatography. In the similar manner as used above in connection with 3-hydroxy-6-substituted picolinic acid, these rearrangement products can be deacylated to give compounds of formulae (27) and (28), and, subsequently, alkylation or haloalkylation of hydroxyl at the 6-position or 5-position are carried out to give a 6-substituted compound of formula (29) and a 5-substituted compound of formula (30).

Next, deesterification can be carried out by a conventional method to give a 6-substituted picolinic acid of formula (31) and a 5-substituted picolinic acid of formula (32) or an acid addition salt thereof. Thereafter, if necessary, the removal of the protective group for hydroxyl at the 3-position can be carried out by a conventional method to give a 4,6-disubstituted 3-hydroxypicolinic acid of formula (33) and a 4,5-disubstituted 3-hydroxypicolinic acid of formula (34) or an acid addition salt thereof.

The picolinic acid derivatives of formula (2), except for the case where $R_1$ represents hydrogen or 4-methoxy, are novel compounds. Further, the picolinamide derivatives of formulae (5) to (7) have high harmful organism control activity and thus are very useful as an intermediate for the synthesis of drugs and agricultural chemicals.

The amines of formula (4) are commercially available or may be produced by a conventional process.

The reaction mixture containing the contemplated compound of the present invention can be purified by extraction, concentration, filtration, chromatography, recrystallization and other conventional means.

According to a preferred embodiment of the present invention, the picolinic acid derivatives of formula (2) and salts thereof may be produced by oxidizing a substituted 2-hydroxymethylpyridine in an inert solvent to give a 2-carboxyl compound and then optionally removing the protective group by catalytic hydrogenation or hydrolysis. In this case, compounds of formula (2), wherein $R_1$ represents 4-methoxy and $R_4$ represents benzyl, are excluded from the scope of the present invention.

Further, according to a preferred embodiment of the present invention, the picolinic acid derivatives of formula (2) and salts thereof may be produced by optionally introducing a protective group into hydroxypicolinic acid, converting the compound to an N-oxide compound, successively performing acylation and rearrangement to introduce acyloxy at the 6-position, and then optionally removing the protective group. In this case, $R_1$ represents alkoxy having 1 to 4 carbon atoms or haloalkoxy having 1 to 4 carbon atoms which has been substituted at the 6-position.

Further, according to a preferred embodiment of the present invention, the picolinic acid derivatives of formula (2) and salts thereof may be produced by optionally introducing a protective group into 3,4-disubstituted picolinic acid, converting the compound to an N-oxide compound, successively performing acylation and rearrangement to introduce acyloxy at the 6-position or 5-position and then optionally removing the protective group. In this case, $R_1$ represents alkoxys having 1 to 4 carbon atoms or haloalkoxys having 1 to 4 carbon atoms which may be the same or different and are substituted at the 4- and 5-positions or the 4- and 6-positions.

EXAMPLES

The following examples of picolinic acid derivatives represented by formulae (1) and (2) according to the present invention and salts thereof, preparation examples, and evaluation test examples further illustrate the present invention, but should not be construed as limiting the scope of the present invention. It should be noted that the examples of the present invention are illustrative only and conventional means may be applied according to the properties of the picolinic acid derivatives clarified by the present invention to perform synthesis, extraction, purification, and utilization.

Production Examples

Example 1

3-Hydroxy-4'-phenoxypicolinanilide

3-Hydroxypicolinic acid (1.39 g, 10.0 mmol) and 1.95 g (12.0 mmol) of carbonyldiimidazole were mixed into anhydrous N,N-dimethylformamide (hereinafter referred to as "DMF") to prepare a suspension (30 ml). An anhydrous DMF solution (25 ml) of 1.85 g (10.0 mmol) of 4-phenoxyaniline was added dropwise to this suspension, and the reaction was allowed to proceed at room temperature overnight. Water (50 ml) was added to the reaction mixture, followed by extraction with ethyl acetate. The organic layer was dried over anhydrous sodium sulfate, and the dried organic layer was concentrated under the reduced pressure. The residue was purified by column chromatography on silica gel (ethyl acetate-n-hexane) to give 1.24 g (yield 41%) of the title compound.

Example 2

3-Hydroxy-4'-benzylpicolinanilide

The procedure of Example 1 was repeated, except that 4-phenoxyaniline was changed to 4-benzylaniline. Thus, the title compound was prepared.

Example 3

3-Hydroxy-4'-(2",6"-di-sec-butylphenoxy)picolinanilide

The procedure of Example 1 was repeated, except that 4-phenoxyaniline was changed to 4-(2',6'-di-sec-butylphenoxy)aniline. Thus, the title compound was prepared.

Example 4

3-Hydroxy-4'-(4"-t-butylphenoxy)picolinanilide

The procedure of Example 1 was repeated, except that 4-phenoxyaniline was changed to 4-(4'-t-butylphenoxy)aniline. Thus, the title compound was prepared.

Example 5

3-Hydroxy-4'-(2",4"-di-t-butylphenoxy)picolinanilide

The procedure of Example 1 was repeated, except that 4-phenoxyaniline was changed to 4-(2',4'-di-t-butylphenoxy)aniline. Thus, the title compound was prepared.

Example 6

3-Hydroxy-4'-(3"-trifluoromethylphenoxy)picolinanilide

The procedure of Example 1 was repeated, except that 4-phenoxyaniline was changed to 4-(3'-trifluoromethylphenoxy)aniline. Thus, the title compound was prepared.

Example 7

3-Hydroxy-N-cyclohexylpicolinamide

The procedure of Example 1 was repeated, except that 4-phenoxyaniline was changed to cyclohexylamine. Thus, the title compound was prepared.

Example 8

3-Benzyloxy-4-methoxy-4'-phenoxypicolinanilide

3-Benzyloxy-4-methoxypicolinic acid (0.65 g, 2.5 mmol) and 0.50 g (3.0 mmol) of carbonyldiimidazole were mixed into anhydrous DMF to prepare a suspension (8 ml). An anhydrous DMF solution (2 ml) of 0.56 g (3.0 mmol) of 4-phenoxyaniline was added dropwise to this suspension, and a reaction was allowed to proceed at room temperature overnight. Water (10 ml) was added to the reaction mixture, followed by extraction with ethyl acetate. The organic layer was dried over anhydrous sodium sulfate, and the dried organic layer was concentrated under the reduced pressure. The residue was purified by column chromatography on silica gel (ethyl acetate-n-hexane) to give 0.76 g (yield 71%) of the title compound.

Example 9

3-Hydroxy-4-methoxy-4'-phenoxypicolinanilide

3-Benzyloxy-4-methoxy-4'-phenoxypicolinanilide (0.64 g, 1.5 mmol) was mixed with ethanol (4 ml) to prepare a suspension. To this suspension was added 64 mg of 10% palladium-carbon. The mixture was subjected to catalytic reduction under atmospheric conditions overnight. The reaction solution was filtered, and the filtrate was concentrated under the reduced pressure. The residue was dissolved in a water-methanol mixed solution, and was recrystallized to give 0.41 g (yield 81%) of the title compound.

Example 10

3-Hydroxy-4-methoxy-4'-(4"-t-butylphenoxy)picolinanilide

The procedure of Examples 8 and 9 was repeated, except that 4-phenoxyaniline was changed to 4-(4'-t-butylphenoxy)aniline. Thus, the title compound was prepared.

Example 11

3-Hydroxy-4-methoxy-3'-phenoxypicolinanilide

The procedure of Examples 8 and 9 was repeated, except that 4-phenoxyaniline was changed to 3-phenoxyaniline. Thus, the title compound was prepared.

Example 12

3-Hydroxy-4-methoxy-2'-phenoxypicolinanilide

The procedure of Examples 8 and 9 was repeated, except that 4-phenoxyaniline was changed to 2-phenoxyaniline. Thus, the title compound was prepared.

Example 13

3-Hydroxy-4-methoxy-4'-benzylpicolinanilide

The procedure of Examples 8 and 9 was repeated, except that 4-phenoxyaniline was changed to 4-benzylaniline. Thus, the title compound was prepared.

Example 14

3-Hydroxy-4-methoxy-4'-phenylthiopicolinanilide

The procedure of Examples 8 and 9 was repeated, except that 4-phenoxyaniline was changed to 4-phenylthioaniline. Thus, the title compound was prepared.

Example 15

3-Hydroxy-4-methoxy-4'-(4"-methoxyphenoxy)picolinanilide

The procedure of Examples 8 and 9 was repeated, except that 4-phenoxyaniline was changed to 4-(4'-methoxyphenoxy)aniline. Thus, the title compound was prepared.

Example 16

3-Hydroxy-4-methoxy-3'-trifluoromethyl-4'-(4"-trifluoromethylphenoxy)picolinanilide The procedure of Examples 8 and 9 was repeated, except that 4-phenoxyaniline was changed to 3-trifluoromethyl-4-(4'-trifluoromethylphenoxy)aniline. Thus, the title compound was prepared.

Example 17

3-Hydroxy-4-methoxy-4'-(4"-phenylphenoxy)picolinanilide

The procedure of Examples 8 and 9 was repeated, except that 4-phenoxyaniline was changed to 4-(4'-phenylphenoxy)aniline. Thus, the title compound was prepared.

Example 18

3-Hydroxy-4-methoxy-4'-(4"-methylphenoxy)picolinanilide

The procedure of Examples 8 and 9 was repeated, except that 4-phenoxyaniline was changed to 4-(4'-methylphenoxy)aniline. Thus, the title compound was prepared.

Example 19

3-Hydroxy-4-methoxy-4'-(4"-methylphenoxy)-3'-trifluoromethylpicolinanilide

The procedure of Examples 8 and 9 was repeated, except that 4-phenoxyaniline was changed to 4-(4'-methylphenoxy)-3-trifluoromethylaniline. Thus, the title compound was prepared.

Example 20

3-Hydroxy-4-methoxy-2'-methoxy-4'-phenoxypicolinanilide

The procedure of Examples 8 and 9 was repeated, except that 4-phenoxyaniline was changed to 2-methoxy-4-phenoxyaniline. Thus, the title compound was prepared.

Example 21

3-Hydroxy-4-methoxy-3'-chloro-4'-phenoxypicolinanilide

The procedure of Examples 8 and 9 was repeated, except that 4-phenoxyaniline was changed to 3-chloro-4-phenoxyaniline. Thus, the title compound was prepared.

Example 22

3-Hydroxy-4-methoxy-4'-phenoxy-3'-trifluoromethylpicolinanilide

The procedure of Examples 8 and 9 was repeated, except that 4-phenoxyaniline was changed to 4-phenoxy-3-trifluoromethylaniline. Thus, the title compound was prepared.

Example 23

3-Hydroxy-4-methoxy-3'-methyl-4'-phenoxypicolinanilide

The procedure of Examples 8 and 9 was repeated, except that 4-phenoxyaniline was changed to 3-methyl-4-phenoxyaniline. Thus, the title compound was prepared.

Example 24

3-Hydroxy-4-methoxy-2'-methoxy-4'-(4"-methylphenoxy)picolinanilide

The procedure of Examples 8 and 9 was repeated, except that 4-phenoxyaniline was changed to 2-methoxy-4-(4'-methylphenoxy)aniline. Thus, the title compound was prepared.

Example 25

3-Hydroxy-4-methoxy-4'-(2",4"-di-t-butyl-phenoxy)picolinanilide

3-Hydroxy-4-methoxypicolinic acid (0.20 g, 1.18 mmol) and 0.23 g (1.42 mmol) of carbonyldiimidazole were mixed into DMF to prepare a suspension (5 ml). An anhydrous DMF solution (1 ml) of 0.35 g (1.18 mmol) of 4-(2',4'-di-t-butylphenoxy)aniline was added dropwise to this suspension, and a reaction was allowed to proceed at room temperature for 2 days. Water (5 ml) was added to the reaction mixture, followed by extraction with ethyl acetate. The organic layer was dried over anhydrous sodium sulfate, and the dried organic layer was concentrated under the reduced pressure. The residue was purified by column chromatography on silica gel (ethyl acetate-n-hexane) to give 0.19 g (yield 36%) of the title compound.

Example 26

3-Hydroxy-4-methoxy-4'-(3"-trifluoromethylphenoxy)picolinanilide 4-(3'-Trifluoromethylphenoxy)aniline (0.15 g, 0.59 mmol) and 0.15 g (0.72 mmol) of dicyclohexylcarbodiimide were added to a suspension (5 ml) of 0.10 g (0.59 mmol) of 3-hydroxy-4-methoxypicolinic acid in anhydrous pyridine, and a reaction was allowed to proceed at 90° C. for 3 hr. The reaction mixture was cooled, and was then filtered. The filtrate was concentrated under the reduced pressure. To the concentrate was added 5 ml of 0.5 M hydrochloric acid. The mixture was vigorously stirred. The resultant precipitate was collected by filtration, was washed with ml of cold water, and was then purified by column chromatography on silica gel (ethyl acetate-n-hexane) to give 0.06 g (yield 25%) of the title compound.

Example 27

3-Hydroxy-4-methoxy-4'-(3",5"-di-t-butyl-phenoxy)picolinanilide

The procedure of Example 26 was repeated, except that 4-(3'-trifluoromethylphenoxy)aniline was changed to 4-(3',5'-di-t-butylphenoxy)aniline. Thus, the title compound was prepared.

Example 28

3-Hydroxy-4-methoxy-3'-chloro-4'-(4"-chlorophenoxy)picolinanilide

The procedure of Example 26 was repeated, except that 4-(3'-trifluoromethylphenoxy)aniline was changed to 3-chloro-4-(4'-chlorophenoxy)aniline. Thus, the title compound was prepared.

Example 29

3-Hydroxy-4-methoxy-4'-(4"-methoxyphenoxy)-3'-methylpicolinanilide 4-(4'-Methoxyphenoxy)aniline (0.23 g, 1.00 mmol), 0.26 g (1.00 mmol) of 3-benzyloxy-4-methoxypicolinic acid, and 0.20 g (1.50 mmol) of 1-hydroxybenzotriazole were mixed into chloroform to prepare a suspension (8 ml). WSCI.HCl (0.29 g, 1.5 mmol), a chloroform solution (4 ml), and 0.15 g (1.5 mmol) of triethylamine were added dropwise at −20° C. to this suspension. Thereafter, a reaction was allowed to proceed at room temperature overnight. The reaction mixture was concentrated under the reduced pressure. The concentrate was dissolved in chloroform. The solution was washed with saturated brine, and was then dried over anhydrous sodium sulfate. The dried solution was concentrated and dried under the reduced pressure. The residue was purified by column chromatography on silica gel (chloroform) to give 0.41 g of 3-benzyloxy-4-methoxy-4'-(4"-methoxyphenoxy)-3'-methylpicolylanilide. This product was suspended in 5 ml of ethanol. To the suspension was added 30 mg of 10% palladium-carbon. The mixture was subjected to catalytic reduction under atmospheric conditions overnight. The reaction solution was filtered, and the filtrate was concentrated under the reduced pressure. The residue was then purified by column chromatography on silica gel (chloroform) to give 0.21 g (yield 55%) of the title compound.

Example 30

3-Hydroxy-4-methoxy-N-(1'-(1-naphthyl)ethyl)picolinamide

The procedure of Example 29 was repeated, except that 4-(4'-methoxyphenoxy)aniline was changed to 1-(1-naphthyl)ethylamine. Thus, the title compound was prepared.

Example 31

3-Hydroxy-4-methoxy-3'-chloro-4'-(4"-methoxyphenoxy)picolinanilide

The procedure of Example 29 was repeated, except that 4-(4'-methoxyphenoxy)aniline was changed to 3-chloro-4-(4'-methoxyphenoxy)aniline. Thus, the title compound was prepared.

Example 32

3-Hydroxy-4-methoxy-3'-chloro-4'-(4"-methylphenoxy)picolinanilide

The procedure of Example 29 was repeated, except that 4-(4'-methoxyphenoxy)aniline was changed to 3-chloro-4-(4'-methylphenoxy)aniline. Thus, the title compound was prepared.

Example 33

3-Hydroxy-4-methoxy-3'-methyl-4'-(4"-methylphenoxy)picolinanilide

The procedure of Example 29 was repeated, except that 4-(4'-methoxyphenoxy)aniline was changed to 3-methyl-4-(4'-methylphenoxy)aniline. Thus, the title compound was prepared.

Example 34

3-Hydroxy-4-methoxy-4'-(4"-trifluoromethoxyphenoxy)picolinanilide

The procedure of Example 29 was repeated, except that 4-(4'-methoxyphenoxy)aniline was changed to 4-(4'-trifluoromethoxyphenoxy)aniline. Thus, the title compound was prepared.

Example 35

3-Hydroxy-4-methoxy-4'-(3"-trifluoromethoxyphenoxy)picolinanilide

The procedure of Example 29 was repeated, except that 4-(4'-methoxyphenoxy)aniline was changed to 4-(3'-trifluoromethoxyphenoxy)aniline. Thus, the title compound was prepared.

Example 36

3-Hydroxy-4-methoxy-4'-(4"-methylphenoxy)-2'-trifluoromethylpicolinanilide

The procedure of Example 29 was repeated, except that 4-(4'-methoxyphenoxy)aniline was changed to 4-(4'-methylphenoxy)-2-trifluoromethylaniline. Thus, the title compound was prepared.

Example 37

3-Hydroxy-4-methoxy-2',4'-di(4"-methylphenoxy)picolinanilide

The procedure of Example 29 was repeated, except that 4-(4'-methoxyphenoxy)aniline was changed to 2,4-di(4'-methylphenoxy)aniline. Thus, the title compound was prepared.

Example 38

3-Hydroxy-4-methoxy-3',5'-di-t-butylpicolinanilide

The procedure of Example 29 was repeated, except that 4-(4'-methoxyphenoxy)aniline was changed to 3,5-di-t-butylaniline. Thus, the title compound was prepared.

Example 39

3-Hydroxy-4-methoxy-4'-benzyloxypicolinanilide

4-Benzyloxyaniline hydrochloride (0.21 g, 0.87 mmol), 0.15 g (0.73 mmol) of 3-hydroxy-4-methoxypicolinic acid hydrochloride, 0.15 g (1.10 mmol) of 1-hydroxybenzotriazole, and 0.16 g (1.10 mmol) of triethylamine were mixed into chloroform to prepare a suspension (2 ml). A chloroform solution (2 ml) of WSCI.HCl (0.21 g, 1.10 mmol) and 0.11 g (1.10 mmol) of triethylamine were added dropwise at −20° C. to this suspension, and a reaction was then allowed to proceed at room temperature overnight. The reaction mixture was concentrated under the reduced pressure. The concentrate was redissolved in chloroform. The solution was washed with saturated brine, and was then dried over anhydrous sodium sulfate. The dried solution was concentrated under the reduced pressure. The residue was purified by column chromatography on silica gel (chloroform) to give 0.15 g (yield 59%) of title compound.

Example 40

3-Hydroxy-4-methoxy-3'-benzyloxypicolinanilide

The procedure of Example 39 was repeated, except that 4-benzyloxyaniline hydrochloride was changed to 3-benzyloxyaniline. Thus, the title compound was prepared.

Example 41

3-Hydroxy-4-methoxy-3'-(3-pyridyl)picolinanilide

The procedure of Example 39 was repeated, except that 4-benzyloxyaniline hydrochloride was changed to 3-(3-pyridyl)aniline. Thus, the title compound was prepared.

Example 42

3-Hydroxy-4-methoxy-N-cyclododecylpicolinamide

The procedure of Example 39 was repeated, except that 4-benzyloxyaniline hydrochloride was changed to cyclododecylamine. Thus, the title compound was prepared.

Example 43

3-Hydroxy-4-methoxy-N-cyclooctylpicolinamide

The procedure of Example 39 was repeated, except that 4-benzyloxyaniline hydrochloride was changed to cyclooctylamine. Thus, the title compound was prepared.

Example 44

3-Hydroxy-4-methoxy-4'-(phenylamino)picolinanilide

The procedure of Example 39 was repeated, except that 4-benzyloxyaniline hydrochloride was changed to 4-phenylaminoaniline. Thus, the title compound was prepared.

Example 45

3-Hydroxy-4-methoxy-N-(1-adamantyl)picolinamide

The procedure of Example 39 was repeated, except that 4-benzyloxyaniline hydrochloride was changed to 1-adamantaneamine. Thus, the title compound was prepared.

Example 46

3-Hydroxy-4-methoxy-4'-(4-morpholinyl)picolinanilide

The procedure of Example 39 was repeated, except that 4-benzyloxyaniline hydrochloride was changed to 4-morpholinoaniline. Thus, the title compound was prepared.

Example 47

3-Hydroxy-4-methoxy-N-(1-adamantanemethyl)picolinamide

The procedure of Example 39 was repeated, except that 4-benzyloxyaniline hydrochloride was changed to 1-adamantanemethylamine. Thus, the title compound was prepared.

Example 48

3-Hydroxy-4-methoxy-3'-methyl-4'-(3"-trifluoromethylphenoxy)picolinanilide

The procedure of Example 39 was repeated, except that 4-benzyloxyaniline hydrochloride was changed to 3-methyl-4-(3'-trifluoromethylphenoxy)aniline. Thus, the title compound was prepared.

Example 49

3-Hydroxy-4-methoxy-4'-cyclohexylpicolinanilide

The procedure of Example 39 was repeated, except that 4-benzyloxyaniline hydrochloride was changed to 4-cyclohexylaniline. Thus, the title compound was prepared.

Example 50

3-Hydroxy-4-methoxy-N-(4'-benzo-15-crown-5-yl)picolinamide

The procedure of Example 39 was repeated, except that 4-benzyloxyaniline hydrochloride was changed to 4'-aminobenzo-15-crown-5. Thus, the title compound was prepared.

Example 51

3-Hydroxy-4-methoxy-(3',4'-ethylenedioxy)picolinanilide

The procedure of Example 39 was repeated, except that 4-benzyloxyaniline hydrochloride was changed to 3,4-ethylenedioxyaniline. Thus, the title compound was prepared.

Example 52

3-Hydroxy-4-methoxy-N-(1'-benzylpiperidin-4'-yl)picolinamide

The procedure of Example 39 was repeated, except that 4-benzyloxyaniline hydrochloride was changed to 4-amino-1-benzylpiperidine. Thus, the title compound was prepared.

Example 53

3-Hydroxy-4-methoxy-N-(2'-(1-cyclohexenyl)ethyl)picolinamide

The procedure of Example 39 was repeated, except that 4-benzyloxyaniline hydrochloride was changed to 2-(1-cyclohexenyl)ethylamine. Thus, the title compound was prepared.

Example 54

3-Hydroxy-4-methoxy-4'-(4''-nitrophenoxy)picolinanilide

The procedure of Example 39 was repeated, except that 4-benzyloxyaniline hydrochloride was changed to 4-(4'-nitrophenoxy)aniline. Thus, the title compound was prepared.

Example 55

3-Hydroxy-4-methoxy-2',6'-dimethyl-4'-phenoxypicolinanilide

The procedure of Example 39 was repeated, except that 4-benzyloxyaniline hydrochloride was changed to 2,6-dimethyl-4-phenoxyaniline. Thus, the title compound was prepared.

Example 56

(2'-Trans)-3-hydroxy-4-methoxy-N-(2'-phenylcyclopropyl)picolinamide

The procedure of Example 39 was repeated, except that 4-benzyloxyaniline hydrochloride was changed to trans-2-phenylcyclopropylamine hydrochloride. Thus, the title compound was prepared.

Example 57

3-Hydroxy-4-methoxy-N-cycloheptylpicolinamide

The procedure of Example 39 was repeated, except that 4-benzyloxyaniline hydrochloride was changed to cycloheptylamine. Thus, the title compound was prepared.

Example 58

3-Hydroxy-4-methoxy-4'-(4''-N-isopropylaminophenoxy)picolinanilide

The procedure of Example 39 was repeated, except that 4-benzyloxyaniline hydrochloride was changed to 4-(4'-N-isopropylaminophenoxy)aniline. Thus, the title compound was prepared.

Example 59

3-Hydroxy-4-methoxy-N-cyclohexylpicolinamide

The procedure of Example 39 was repeated, except that 4-benzyloxyaniline hydrochloride was changed to cyclohexylamine. Thus, the title compound was prepared.

Example 60

3-Hydroxy-4-methoxypicolinanilide

The procedure of Example 39 was repeated, except that 4-benzyloxyaniline hydrochloride was changed to aniline. Thus, the title compound was prepared.

Example 61

3-Hydroxy-4-methoxy-4'-chloropicolinanilide

The procedure of Example 39 was repeated, except that 4-benzyloxyaniline hydrochloride was changed to 4-chloroaniline. Thus, the title compound was prepared.

Example 62

3-Hydroxy-4-methoxy-4'-(4''-aminophenoxy)picolinanilide

The procedure of Example 39 was repeated, except that 4-benzyloxyaniline hydrochloride was changed to 4-(4'-aminophenoxy)aniline. Thus, the title compound was prepared.

Example 63

3-Hydroxy-4-methoxy-N-(2'-cyclohexylethyl)picolinamide

The procedure of Example 39 was repeated, except that 4-benzyloxyaniline hydrochloride was changed to 2-cyclohexylethylamine. Thus, the title compound was prepared.

Example 64

3-Hydroxy-4-methoxy-4'-benzoylpicolinanilide

The procedure of Example 39 was repeated, except that 4-benzyloxyaniline hydrochloride was changed to 4-aminobenzophenone. Thus, the title compound was prepared.

Example 65

3-Hydroxy-4-methoxy-N-(1-indanyl)picolinamide

The procedure of Example 39 was repeated, except that 4-benzyloxyaniline hydrochloride was changed to 1-aminoindan. Thus, the title compound was prepared.

Example 66

3-Hydroxy-4-methoxy-N-(1',2',31,4'-tetrahydro-naphtho-1'-yl)picolinamide

The procedure of Example 39 was repeated, except that 4-benzyloxyaniline hydrochloride was changed to 1,2,3,4-tetrahydro-1-naphthylamine. Thus, the title compound was prepared.

Example 67

3-Hydroxy-4-methoxy-N-benzylpicolinamide

The procedure of Example 39 was repeated, except that 4-benzyloxyaniline hydrochloride was changed to benzylamine. Thus, the title compound was prepared.

Example 68

3-Hydroxy-4-methoxy-N-phenetylpicolinamide

The procedure of Example 39 was repeated, except that 4-benzyloxyaniline hydrochloride was changed to phenetylamine. Thus, the title compound was prepared.

Example 69

3-Hydroxy-4-methoxy-N-(1'-phenylethyl)picolinamide

The procedure of Example 39 was repeated, except that 4-benzyloxyaniline hydrochloride was changed to α-methylbenzylamine. Thus, the title compound was prepared.

Example 70

3-Hydroxy-4-methoxy-N-(1''-methyl-1'-phenylethyl)picolinamide

The procedure of Example 39 was repeated, except that 4-benzyloxyaniline hydrochloride was changed to 1-methyl-1-phenylethylamine. Thus, the title compound was prepared.

Example 71

3-Hydroxy-4-methoxy-N-(4'-phenoxybenzyl)picolinamide

The procedure of Example 39 was repeated, except that 4-benzyloxyaniline hydrochloride was changed to 4-phenoxybenzylamine. Thus, the title compound was prepared.

Example 72

3-Hydroxy-4-methoxy-4'-phenetyloxypicolinanilide

The procedure of Example 39 was repeated, except that 4-benzyloxyaniline hydrochloride was changed to 4-phenetyloxyaniline. Thus, the title compound was prepared.

Example 73

3-Hydroxy-4-methoxy-4'-(4''-isobutyrylpiperazin-1''-yl)picolinanilide

The procedure of Example 39 was repeated, except that 4-benzyloxyaniline hydrochloride was changed to 4-(4'-isobutyrylpiperazin-1'-yl)aniline. Thus, the title compound was prepared.

Example 74

3-Hydroxy-4-methoxy-N-(1'-homopiperidinyl)picolinamide

The procedure of Example 39 was repeated, except that 4-benzyloxyaniline hydrochloride was changed to 1-homopiperidinylamine. Thus, the title compound was prepared.

Example 75

3-Hydroxy-4-methoxy-N-(cyclohexylmethyl)picolinamide

The procedure of Example 39 was repeated, except that 4-benzyloxyaniline hydrochloride was changed to cyclohexylmethylamine. Thus, the title compound was prepared.

Example 76

(2'-Trans)-3-hydroxy-4-methoxy-N-(2'-methylcyclohexyl)picolinamide

The procedure of Example 39 was repeated, except that 4-benzyloxyaniline hydrochloride was changed to trans-2-methylcyclohexylamine. Thus, the title compound was prepared.

Example 77

(2'-Cis)-3-hydroxy-4-methoxy-N-(2'-methylcyclohexyl)picolinamide

The procedure of Example 39 was repeated, except that 4-benzyloxyaniline hydrochloride was changed to cis-2-methylcyclohexylamine. Thus, the title compound was prepared.

Example 78

3-Hydroxy-4-methoxy-N-(4'-methylcyclohexyl)picolinamide

The procedure of Example 39 was repeated, except that 4-benzyloxyaniline hydrochloride was changed to 4-methylcyclohexylamine. Thus, the title compound was prepared.

Example 79

3-Hydroxy-4-methoxy-N-cyclopentylpicolinamide

The procedure of Example 39 was repeated, except that 4-benzyloxyaniline hydrochloride was changed to cyclopentylamine. Thus, the title compound was prepared.

Example 80

3-Hydroxy-4-methoxy-N-cyclopropylpicolinamide

The procedure of Example 39 was repeated, except that 4-benzyloxyaniline hydrochloride was changed to cyclopropylamine. Thus, the title compound was prepared.

Example 81

3-Hydroxy-4-methoxy-N-cyclobutylpicolinamide

The procedure of Example 39 was repeated, except that 4-benzyloxyaniline hydrochloride was changed to cyclobutylamine. Thus, the title compound was prepared.

Example 82

3-Hydroxy-4-methoxy-N-(sec-butyl)picolinamide

The procedure of Example 39 was repeated, except that 4-benzyloxyaniline hydrochloride was changed to sec-butylamine. Thus, the title compound was prepared.

Example 83

3-Hydroxy-4-methoxy-N-(n-hexyl)picolinamide

The procedure of Example 39 was repeated, except that 4-benzyloxyaniline hydrochloride was changed to n-hexylamine. Thus, the title compound was prepared.

Example 84

3-Hydroxy-4-methoxy-N-(4'-hydroxycyclohexyl)picolinamide

The procedure of Example 39 was repeated, except that 4-benzyloxyaniline hydrochloride was changed to 4-hydroxycyclohexylamine. Thus, the title compound was prepared.

Example 85

3-Hydroxy-4-methoxy-N-(2'-hydroxycyclohexyl)picolinamide

The procedure of Example 39 was repeated, except that 4-benzyloxyaniline hydrochloride was changed to 2-hydroxycyclohexylamine. Thus, the title compound was prepared.

Example 86

3-Hydroxy-4-methoxy-N-(n-octyl)picolinamide

The procedure of Example 39 was repeated, except that 4-benzyloxyaniline hydrochloride was changed to n-octylamine. Thus, the title compound was prepared.

Example 87

3-Hydroxy-4-methoxy-N-(n-heptyl)picolinamide

The procedure of Example 39 was repeated, except that 4-benzyloxyaniline hydrochloride was changed to n-heptylamine. Thus, the title compound was prepared.

Example 88

3-Hydroxy-4-methoxy-N-(3',3'-dimethylbutyl)picolinamide

The procedure of Example 39 was repeated, except that 4-benzyloxyaniline hydrochloride was changed to 3,3-dimethylbutylamine. Thus, the title compound was prepared.

Example 89

3-Benzyloxy-6-methoxy-4'-phenoxypicolinanilide

The procedure of Example 29 was repeated, except that 3-benzyloxy-4-methoxypicolinic acid was changed to 3-benzyloxy-6-methoxypicolinic acid. The product was concentrated and dried under the reduced pressure in the same manner as in Example 29. Finally, the residue was purified by column chromatography on silica gel (chloroform). Thus, the title compound was prepared (yield 57%).

Example 90

3-Hydroxy-6-methoxy-4'-phenoxypicolinanilide

3-Benzyloxy-6-methoxy-4'-phenoxypicolinanilide was suspended in 5 ml of ethanol. 10% palladium-carbon (30 mg) was added to the suspension. The mixture was subjected to catalytic reduction under atmospheric conditions overnight. The reaction solution was filtered, and the filtrate was concentrated under the reduced pressure. The residue was then purified by column chromatography on silica gel (chloroform) to give the title compound (yield 83%).

Example 91

3-Hydroxy-6-methoxy-N-cyclohexylpicolinamide

The procedure of Example 29 was repeated, except that 3-benzyloxy-4-methoxypicolinic acid was changed to 3-benzyloxy-6-methoxypicolinic acid and 4-(4'-methoxyphenoxy)aniline was changed to cyclohexylamine. Thus, the title compound was prepared.

Example 92

3-Hydroxy-4,6-dimethoxy-4'-phenoxypicolinanilide

The procedure of Example 29 was repeated, except that 3-benzyloxy-4-methoxypicolinic acid was changed to 3-benzyloxy-4,6-dimethoxypicolinic acid and 4-(4'-methoxyphenoxy)aniline was changed to 4-phenoxyaniline. Thus, the title compound was prepared.

Example 93

3-Hydroxy-4,5-dimethoxy-4'-phenoxypicolinanilide

The procedure of Example 29 was repeated, except that 3-benzyloxy-4-methoxypicolinic acid was changed to 3-benzyloxy-4,5-dimethoxypicolinic acid and 4-(4'-methoxyphenoxy)aniline was changed to 4-phenoxyaniline. Thus, the title compound was prepared.

Example 94

3-Benzyloxy-4-methoxypicolinic acid (1) 3-Hydroxy-2-methyl-4-pyrone (25 g, 0.198 mol) was dissolved in 70 ml of DMF. To the solution was added 8.7 g (0.218 mol) of sodium hydride (60% in mineral oil). The mixture was stirred under ice cooling for 30 min. Benzyl bromide (37.3 g, 0.218 mol) was added dropwise to the reaction solution under ice cooling, and a reaction was allowed to proceed at room temperature overnight. The reaction solution was poured into ice water, followed by extraction with ethyl acetate. The organic layer was washed with water, and was dried over anhydrous sodium sulfate. The solvent was removed by distillation under the reduced pressure. The reddish brown oil thus obtained (64 g) was applied to column chromatography on silica gel (Wako Gel C-200, n-hexane-ethyl acetate) to give 41.6 g (yield 97%) of 3-benzyloxy-2-methyl-4-pyrone.

$^1$H-NMR (CDCl$_3$): δ=2.07 (s, 3H), 5.14 (s, 2H), 6.35 (1H, d), 7.28–7.39 (m, 5H), 7.58 (d, 1H)

(2) 28% aqueous ammonia (100 ml) and 30 ml of ethanol were added to 3-benzyloxy-2-methyl-4-pyrone (40.6 g, 0.188 mol). The mixture was stirred at room temperature for 5 days. The reaction mixture was concentrated under the reduced pressure. The precipitate was filtered, and was then washed with a minor amount of ethyl acetate to give 32.2 g of 3-benzyloxy-2-methyl-4-pyridone as a light yellow crystal. The same compound was also obtained from the filtrate (5.6 g, yield 93%).

$^1$H-NMR (CDCl$_3$): δ=2.13 (s, 3H), 5.02 (s, 2H), 6.32 (d, 1H), 7.22–7.30 (m, 5H), 7.37 (d, 1H), 13.13 (br, 1H)

(3) 3-Benzyloxy-2-methyl-4-pyridone (21.5 g, 0.10 mol) was suspended in methanol-acetonitrile (1:9 v/v, 400 ml). Diisopropylethylamine (18.1 g, 0.14 mol) was added to the suspension. The mixture was then stirred. A 2.0 M solution (70 ml) of tetramethylsilyldiazomethane in n-hexane was added dropwise to the mixture, and a reaction was allowed to proceed at room temperature overnight. The reaction solution was concentrated under the reduced pressure. The concentrate was applied to column chromatography on silica gel (Wako Gel C-200, n-hexane-ethyl acetate) to give 17.3 g (yield 76%) of 3-benzyloxy-4-methoxy-2-methylpyridine.

$^1$H-NMR (CDCl$_3$): δ=2.34 (s, 3H), 3.84 (s, 3H), 4.91 (s, 2H), 6.66 (1H,d), 7.24–7.38 (m, 5H), 8.08 (d, 1H)

(4) 3-Benzyloxy-4-methoxy-2-methylpyridine (23.0 g) was dissolved in 200 ml of dichloromethane. m-Chloroperbenzoic acid (20.7 g) was added to the solution under ice cooling, and a reaction was allowed to proceed at room temperature overnight. The reaction product was washed with an aqueous saturated sodium hydrogensulfite solution and an aqueous saturated sodium hydrogencarbonate solution, and the washed reaction product was dried over anhydrous sodium sulfate. The solvent was concentrated under the reduced pressure. Acetic anhydride (200 ml) was added to 35.5 g of the concentrate as a light yellow oil, and a reaction was allowed to proceed at 100° C. for one hr. Ethanol (100 ml) was then added thereto, and the mixture was further refluxed for one hr. The reaction solution was concentrated under the reduced pressure. A 2 M solution (200 ml) of sodium hydroxide in 50% methanol was added to the concentrate, and the mixture was stirred at 80° C. for one hr. The reaction solution was concentrated under the reduced pressure. The concentrate was extracted with chloroform. The extract was washed with saturated brine, and was then dried over anhydrous sodium sulfate, followed by concentration under the reduced pressure to give 19.6 g (yield 80%) of 3-benzyloxy-2-hydroxymethyl-4-methoxypyridine as a yellowish brown solid.

$^1$H-NMR (CDCl$_3$): δ=3.89 (s, 3H), 4.56 (s, 2H), 4.97 (s, 2H), 6.77 (d, 1H), 7.24–7.36 (m, 5H), 8.15 (d, 1H)

(5) 3-Benzyloxy-2-hydroxymethyl-4-methoxypyridine (7.1 g) and 2.5 g of potassium hydroxide were suspended in 100 ml of water. While heating the suspension in a water bath, potassium permanganate (7.3 g) was added thereto, and the mixture was stirred. The precipitate was filtered, and was washed with 100 ml of methanol. The filtrate and the washings were combined, followed by concentration under the reduced pressure. The concentrate was adjusted to pH 1 by the addition of concentrated hydrochloric acid. The precipitate was filtered, washed with water, and then dried to give 6.3 g (yield 83.9%) of the title compound as colorless powder.

Example 95

3-Hydroxy-4-methoxypicolinic acid

3-Benzyloxy-4-methoxypicolinic acid (5.3 g) was suspended in 25 ml of ethanol. 10% palladium-carbon (0.5 g) was added to the suspension. The mixture was then catalytically hydrogenated under atmospheric pressure for 30 min. The reaction solution was filtered under the reduced pressure. The filtrate was concentrated under the reduced pressure to give 2.8 g (yield 81.6%) of the title compound as colorless powder.

Example 96

3-Hydroxy-4-methoxypicolinic acid hydrochloride

3-Benzyloxy-4-methoxypicolinic acid (8.3 g) was dissolved in 100 ml of methanol. Concentrated hydrochloric acid (2 ml) was added to the solution. The mixture was heated under reflux for 30 min. The reaction solution was concentrated under the reduced pressure. The residue was recrystallized from water-ethanol to give 3.6 g (yield 54.8%) of title compound as colorless powder.

Example 97

Methyl 3-benzyloxy-6-methoxy-picolinate (1) 3-Hydroxypicolinic acid (5.0 g) was dissolved in 350 ml of toluene and 100 ml of methanol. A 2 M solution (25 ml) of trimethylsilyldiazomethane in hexane was added dropwise to the solution, and a reaction was allowed to proceed at room temperature overnight. The reaction solution was concentrated under the reduced pressure. Methylene chloride (100 ml) and water (100 ml) were then added to the concentrate to conduct extraction. The aqueous layer was then extracted with methylene chloride. The organic layer was dried over magnesium sulfate, and was concentrated under the reduced pressure. The residue was purified by column chromatography on silica gel (ethyl acetate-hexane) to give 2.3 g (yield 41%) of methyl 3-hydroxypicolinate.

$^1$H-NMR (CDCl$_3$): δ=4.06 (s, 3H), 7.37 (dd, 1H), 7.43 (dd, 1H), 8.28 (dd, 1H)

(2) Methyl 3-hydroxypicolinate (2.0 g) was dissolved in 100 ml of acetone. Potassium carbonate (3.4 g) and 3.4 ml of benzyl bromide were added to the solution, and a reaction was allowed to proceed at room temperature overnight. The reaction solution was then refluxed for 4 hr. Water (50 ml) was added thereto, and the mixture was neutralized with 1 N hydrochloric acid, followed by concentration under the reduced pressure. Methylene chloride and water were added to the residue. The organic layer was dried over magnesium sulfate, and was then dried under the reduced pressure. The dried organic layer was then purified by column chromatography (chloroform-methanol) to give 2.1 g (yield 62%) of methyl 3-benzyloxypicolinate.

$^1$H-NMR (CDCl$_3$): δ=3.99 (s, 3H), 5.22 (s, 2H), 7.29–7.48 (m, 7H), 8.29 (t, 1H)

(3) Methyl 3-benzyloxypicolinate (2.0 g) was converted to N-oxide in the same manner as in Example 94, followed by acetylation to give methyl 6-acetoxy-3-benzyloxypicolinate which was then hydrolyzed with an alkali to give 0.77 g (yield 36%) of methyl 3-benzyloxy-6-hydroxy-picolinate.

$^1$H-NMR (CDCl$_3$): δ=3.93 (s, 3H), 5.06 (s, 2H), 6.77 (d, 1H), 7.34–7.44 (m, 6H)

(4) Methyl 3-benzyloxy-6-hydroxy-picolinate (0.55 g) was dissolved in 55 ml of acetone and 20 ml of methyl iodide. Potassium carbonate (1.4 g) was added to the solution, and the mixture was refluxed for 3 hr. After cooling, the reaction solution was neutralized with 1 N hydrochloric acid, and was concentrated under the reduced pressure. Methylene chloride and water were then added to the concentrate to conduct extraction. The organic layer was dried over magnesium sulfate, and the dried organic layer was then concentrated under the reduced pressure. The residue was purified by column chromatography (chloroform-methanol) to give 0.28 g (yield 49%) of the title compound.

Example 98

3-Benzyloxy-6-methoxy-picolinic acid

Methyl 3-benzyloxy-6-methoxy-picolinate (20 mg) was dissolved in 1 ml of methanol. A 1 N aqueous sodium hydroxide solution (0.33 ml) was added to the solution, and a reaction was allowed to proceed at room temperature for 3 hr. The reaction solution was then adjusted to pH 3 by the addition of 1 N hydrochloric acid. The precipitate was collected by filtration to give 12 mg (yield 63%) of the title compound.

Example 99

Methyl 3-hydroxy-6-methoxy-picolinate

10% palladium-carbon (48 mg) was added to 480 mg of methyl 3-benzyloxy-6-methoxy-picolinate. After the replacement of the atmosphere by nitrogen, 25 ml of methanol was added thereto. Further, after the replacement of the atmosphere by hydrogen, the mixture was vigorously stirred to allow a reaction to proceed. One hr after the initiation of the reaction, the reaction mixture was filtered, followed by purification by chromatography on silica gel (chloroform-methanol) to give 240 mg (yield 76%) of the title compound.

Example 100

3-Hydroxy-6-methoxypicolinic acid

Methyl 3-hydroxy-6-methoxypicolinate (80 mg) was dissolved in 4 ml of methanol. A 1 N aqueous sodium hydroxide solution (2 ml) was added to the solution, and a reaction was allowed to proceed at room temperature for 3 hr. The reaction solution was adjusted to pH 3 by the addition of 1 N hydrochloric acid. The precipitate was collected by filtration to give 56 mg (yield 76%) of the title compound.

Example 101

Methyl 3-benzyloxy-4,6-dimethoxypicolinate (1) 3-Benzyloxy-4-methoxypicolinic acid (the compound of Example 94) (1 g) was converted to a methyl ester in the same manner as in Example 97 to give 0.86 g (yield 81%) of methyl 3-benzyloxy-4-methoxypicolinate.

$^1$H-NMR (CDCl$_3$): δ=3.82 (s, 3H), 3.83 (s, 3H), 5.02 (s, 2H), 6.86 (d, 1H), 7.19–7.41 (m, 5H), 8.22 (d, 1H)

(2) Methyl 3-benzyloxy-4-methoxypicolinate (0.80 g) was oxidized with m-chloroperbenzoic acid in the same manner as in Example 94 to give 0.69 g (yield 81%) of methyl-N-oxide 3-benzyloxy-4-methoxypicolinate.

$^1$H-NMR (CDCl$_3$): δ=3.83 (s, 3H), 3.86H (s, 3H), 5.04 (s, 2H), 6.74 (d, 1H), 7.19–7.41 (m, 5H), 7.91 (d, 1H)

(3) Methyl-N-oxide 3-benzyloxy-4-methoxypicolinate (672 mg) was dissolved in 33.6 ml of acetic anhydride, and a reaction was allowed to proceed at 100° C. overnight, followed by concentration under the reduced pressure. The concentrate was purified by chromatography on silica gel (ethyl acetate-hexane=1:1) to give 173 mg (yield 22%) of methyl 6-acetoxy-3-benzyloxy-4-methoxypicolinate and 87 mg (yield 11%) of methyl 5-acetoxy-3-benzyloxy-4-methoxypicolinate.

Methyl 6-acetoxy-3-benzyloxy-4-methoxypicolinate
$^1$H-NMR (CDCl$_3$): δ=2.25 (s, 3H), 3.82 (s, 3H), 3.88 (s, 3H), 5.02 (s, 2H), 6.71 (s, 1H), 7.19–7.43 (m, 5H)

Methyl 5-acetoxy-3-benzyloxy-4-methoxypicolinate
$^1$H-NMR (CDCl$_3$): δ=2.37 (s, 3H), 3.92 (s, 3H), 4.00 (s, 3H), 5.10 (s, 2H), 7.19–7.43 (m, 5H), 8.19 (s, 1H)

(4) Methyl 6-acetoxy-3-benzyloxy-4-methoxypicolinate was hydrolized with an alkali in the same manner as in Example 97 to give 96 mg (yield 85%) of methyl 3-benzyloxy-6-hydroxy-4-methoxypicolinate.

¹H-NMR (CDCl₃): δ=3.80 (s, 3H), 3.81 (s, 3H), 4.87 (s, 2H), 6.04 (s, 1H), 7.19–7.37 (m, 5H), 9.39 (br, 1H)

(5) Methyl 3-benzyloxy-6-hydroxy-4-methoxypicolinate (90 mg) was methylated in the same manner as in Example 97 to give 33 mg (yield 35%) of the title compound.

Example 102

3-Benzyloxy-4,6-dimethoxypicolinic acid

Methyl 3-benzyloxy-4,6-dimethoxypicolinate (33 mg) was dissolved in 2 ml of methanol. A 1 N aqueous sodium hydroxide solution (0.54 ml) was added to the solution, and a reaction was allowed to proceed at room temperature for 4 hr. The reaction solution was neutralized with 1 N hydrochloric acid, and was then concentrated under the reduced pressure to give the title compound.

Example 103

Methyl 3-benzyloxy-4,5-dimethoxypicolinate (1) Methyl 5-acetoxy-3-benzyloxy-4-methoxypicolinate (87 mg) was hydrolyzed with an alkali in the same manner as in Example 101 to give 71 mg (yield 93%) of methyl 3-benzyloxy-5-hydroxy-4-methoxypicolinate.

¹H-NMR (CDCl₃): δ=3.84 (s, 3H), 3.98 (s, 3H), 5.01 (s, 2H), 7.19–7.42 (m, 5H), 8.12 (s, 1H)

(2) The procedure of Example 101 was repeated, except that 71 mg of methyl 3-benzyloxy-5-hydroxy-4-methoxypicolinate was used. Thus, 21 mg (yield 28%) of the title compound was prepared.

Example 104

3-Benzyloxy-4,5-dimethoxypicolinic acid

Methyl 3-benzyloxy-4,5-dimethoxypicolinate (20 mg) was dissolved in 1 ml of methanol. A 1 N aqueous sodium hydroxide solution (0.33 ml) was added to the solution, and a reaction was allowed to proceed at room temperature for 3 hr. The reaction solution was neutralized with 1 N hydrochloric acid, and was then concentrated under the reduced pressure to give the title compound.

Example 105

3-Hydroxy-4-methoxy-4'-(2"-phenoxyethyloxy)picolinanilide

The procedure of Example 29 was repeated, except that 4-(4'-methoxyphenoxy)aniline was changed to 4-(2'-phenoxyethyloxy)aniline. Thus, the title compound was prepared.

Example 106

(1'R)-3-Hydroxy-4-methoxy-N-(1'-phenylethyl)picolinamide

The procedure of Example 29 was repeated, except that 4-(4'-methoxyphenoxy)aniline was changed to (R)-(+)-α-methylbenzene. Thus, the title compound was prepared.

Example 107

(1'S)-3-Hydroxy-4-methoxy-N-(1'-phenylethyl)picolinamide

The procedure of Example 29 was repeated, except that 4-(4'-methoxyphenoxy)aniline was changed to (S)-(–)-α-methylbenzylamine. Thus, the title compound was prepared.

Example 108

3-Hydroxy-4-methoxy-N-1',1',3',3'-tetramethylbutylpicolinamide

The procedure of Example 29 was repeated, except that 4-(4'-methoxyphenoxy)aniline was changed to 1,1,3,3-tetramethylbutylamine. Thus, the title compound was prepared.

Example 109

3-Hydroxy-4-methoxy-4'-(3"-phenylpropyloxy)picolinanilide

The procedure of Example 29 was repeated, except that 4-(4'-methoxyphenoxy)aniline was changed to 4-(3'-phenylpropyloxy)aniline. Thus, the title compound was prepared.

Example 110

3-Hydroxy-4-methoxy-(3'-chloro-4'-phenetyloxy)picolinanilide

The procedure of Example 29 was repeated, except that 4-(4'-methoxyphenoxy)aniline was changed to 3-chloro-4-phenetyloxyaniline. Thus, the title compound was prepared.

Example 111

3-Hydroxy-4-methoxy-N-(2',5'-dichloropentyl)picolinamide

The procedure of Example 29 was repeated, except that 4-(4'-methoxyphenoxy)aniline was changed to 1-amino-2,5-dichloropentane. Thus, the title compound was prepared.

Example 112

3-Hydroxy-4-methoxy-N-3'-phenylpropylpicolinamide

The procedure of Example 29 was repeated, except that 4-(4'-methoxyphenoxy)aniline was changed to 3-phenyl-1-propylamine. Thus, the title compound was prepared.

Example 113

3-Hydroxy-4-methoxy-N-4'-phenylbutylpicolinamide

The procedure of Example 29 was repeated, except that 4-(4'-methoxyphenoxy)aniline was changed to 4-phenylbutylamine. Thus, the title compound was prepared.

Example 114

3-Hydroxy-4-methoxy-4'-t-butylpicolinanilide

The procedure of Example 29 was repeated, except that 4-(4'-methoxyphenoxy)aniline was changed to 4-t-butylaniline. Thus, the title compound was prepared.

Example 115

3-Hydroxy-4-methoxy-4'-trifluoromethylpicolinanilide

The procedure of Example 29 was repeated, except that 4-(4'-methoxyphenoxy)aniline was changed to 4-trifluoromethylaniline. Thus, the title compound was prepared.

Example 116

3-Hydroxy-4-methoxy-4'-trifluoromethoxypicolinanilide

The procedure of Example 29 was repeated, except that 4-(4'-methoxyphenoxy)aniline was changed to 4-trifluoromethoxyaniline. Thus, the title compound was prepared.

Example 117

(1'S)-3-Hydroxy-4-methoxy-N-(1'-cyclohexylethyl)picolinamide

The procedure of Example 29 was repeated, except that 4-(4'-methoxyphenoxy)aniline was changed to (S)-(+)-1-cyclohexylethylamine. Thus, the title compound was prepared.

Example 118

(1'R)-3-Hydroxy-4-methoxy-N-(1'-cyclohexylethyl)picolinamide

The procedure of Example 29 was repeated, except that 4-(4'-methoxyphenoxy)aniline was changed to (R)-(−)-1-cyclohexylethylamine. Thus, the title compound was prepared.

Example 119

3-Hydroxy-4-methoxy-4'-(4"-chlorophenetyloxy)picolinanilide

The procedure of Example 29 was repeated, except that 4-(4'-methoxyphenoxy)aniline was changed to 4-(4'-chlorophenetyloxy)aniline. Thus, the title compound was prepared.

Example 120

3-Hydroxy-4-methoxy-4'-fluoropicolinanilide

The procedure of Example 29 was repeated, except that 4-(4'-methoxyphenoxy)aniline was changed to 4-fluoroaniline. Thus, the title compound was prepared.

Example 121

3-Hydroxy-4-methoxy-2'-fluoro-4'-methylpicolinanilide

The procedure of Example 29 was repeated, except that 4-(4'-methoxyphenoxy)aniline was changed to 2-fluoro-4-methylaniline. Thus, the title compound was prepared.

Example 122

3-Hydroxy-4-methoxy-3',5'-difluoropicolinanilide

The procedure of Example 29 was repeated, except that 4-(4'-methoxyphenoxy)aniline was changed to 3,5-difluoroaniline. Thus, the title compound was prepared.

Example 123

3-Hydroxy-4-methoxy-4'-methylpicolinanilide

The procedure of Example 29 was repeated, except that 4-(4'-methoxyphenoxy)aniline was changed to 4-methylaniline. Thus, the title compound was prepared.

Example 124

3-Hydroxy-4-methoxy-4'-(3"-phenoxypropyloxy)picolinanilide

The procedure of Example 29 was repeated, except that 4-(4'-methoxyphenoxy)aniline was changed to 4-(3'-phenoxypropyloxy)aniline. Thus, the title compound was prepared.

Example 125

3-Hydroxy-4-methoxy-4'-neopentylpicolinanilide

The procedure of Example 29 was repeated, except that 4-(4'-methoxyphenoxy)aniline was changed to 4-neopentylaniline. Thus, the title compound was prepared.

Example 126

3-Hydroxy-4-methoxy-N-(2-pyridyl)picolinamide

The procedure of Example 29 was repeated, except that 4-(4'-methoxyphenoxy)aniline was changed to 2-aminopyridine. Thus, the title compound was prepared.

Example 127

3-Hydroxy-4-methoxy-3',4'-dichloropicolinanilide

The procedure of Example 29 was repeated, except that 4-(4'-methoxyphenoxy)aniline was changed to 3,4-dichloroaniline. Thus, the title compound was prepared.

Example 128

3-Hydroxy-4-methoxy-4'-t-butyl-2',6'-dimethyl-picolinanilide

The procedure of Example 29 was repeated, except that 4-(4'-methoxyphenoxy)aniline was changed to 4-t-butyl-2,6-dimethylaniline. Thus, the title compound was prepared.

Example 129

3-Hydroxy-4-methoxy-4'-t-butyl-2'-chloropicolinanilide

The procedure of Example 29 was repeated, except that 4-(4'-methoxyphenoxy)aniline was changed to 4-t-butyl-2-chloroaniline. Thus, the title compound was prepared.

Example 130

3-Hydroxy-4-methoxy-N-(5'-t-butylisoxazol-3'-yl)picolinamide

The procedure of Example 29 was repeated, except that 4-(4'-methoxyphenoxy)aniline was changed to 3-amino-5-t-butylisoxazole. Thus, the title compound was prepared.

Example 131

3-Hydroxy-4-methoxy-N-(4'-t-butylthiazol-2'-yl)picolinamide

The procedure of Example 29 was repeated, except that 4-(4'-methoxyphenoxy)aniline was changed to 2-amino-4-t-butylthiazole. Thus, the title compound was prepared.

Example 132

3-Acetyloxy-4-methoxy-3'-benzyloxypicolinanilide

3-Hydroxy-4-methoxy-3'-benzyloxypicolinanilide (20 mg) was dissolved in 1 ml of acetic anhydride, and a reaction was allowed to proceed at 80° C. for 3 hr. The reaction solution was concentrated under the reduced pressure. The concentrate was extracted with chloroform, followed by washing with a saturated sodium hydrogencarbonate solution and then with saturated brine. The washed extract was then dried over anhydrous sodium sulfate, and was then concentrated under the reduced pressure. The residue was purified by column chromatography on silica gel (chloroform) to give 15 mg (yield 67%) of title compound.

List of Compounds of Production Examples/Results of NMR Measurement

The compounds produced in the above examples were as shown in Tables 1 to 4 below. NMR spectral data (1H-NMRσ (ppm)) on the compounds produced in the examples were as shown in Table 5 below. In Table 5, c, d, m, and w mean solvents for measurement. Specifically, c represents $CDCl_3$, d $DMSO-d_6$ µm methanol-$d_4$, and w $D_2O$.

Production of Preparations

Preparations containing the compounds according to the present invention were prepared according to the following examples.

Preparation Example 1

Emulsifiable Concentrate

Each compound (20 parts by weight) of the present invention produced above was dissolved in 50 parts by weight of xylene and 20 parts by weight of DMF. Polyoxyethylene alkylaryl ether (10 parts by weight) was added to the solution, followed by mixing while stirring. Thus, 20% emulsifiable concentrates were prepared.

Preparation Example 2

Wettable Powder

Each compound (25 parts by weight) of the present invention produced above was added to a mixture of 7 parts by weight of polyoxyethylene alkylaryl ether, 3 parts by weight of calcium ligninsulfonate, 30 parts by weight of clay, and 35 parts by weight of diatomaceous earth, followed by homogeneous mixing while stirring in a juice mixer. Thus, 25% wettable powders were prepared.

Preparation Example 3

Granules

Calcium ligninsulfonate (2 parts by weight), 40 parts by weight of bentonite, and 53 parts by weight of talc were added to and thoroughly mixed with each compound (5 parts by weight) of the present invention produced above while stirring. A suitable amount of water was then added to these mixtures, and the mixtures were stirred and thoroughly kneaded. The kneaded products were then granulated by means of a granulator, followed by forced draft drying to prepare 5% granules.

Preparation Example 4

Dust

Each compound (2 parts by weight) of the present invention produced above was dissolved in a suitable amount of acetone. Talc (37 parts by weight), 1 part by weight of calcium stearate, and 60 parts by weight of clay were added to the solutions, followed by mixing while stirring in a juice mixer. Acetone was removed by evaporation to prepare 2% dusts.

Evaluation Test

The above preparations were evaluated for the control activity against plant pathogenic fungi according to the following test examples.

Test Example 1

Preventive Effect Against Rice Blast

The 20% emulsifiable concentrate prepared in Preparation Example 1 was diluted with water to prepare a test solution having a concentration of 100 ppm. The test solution was applied to stems and leaves of fourth-leaf stage rice seedlings (cultivar: Jikkoku) raised in an environment control room. The rice seedlings, to which the test solution had been applied, were air dried. Thereafter, the rice seedlings were inoculated by spraying with a conidial suspension of rice blast fungi (*Pyricularia oryze*). These rice seedlings were then allowed to stand within an inoculation box kept at a humidity of 100% for 40 hr after the inoculation to render the condition suitable for infection, and were then transferred to an environment controlled greenhouse to induce the disease. Six days after the inoculation, the number of lesions per leaf was counted and compared with the number of lesions per leaf in the nontreated plot to calculate the protective value. The results were evaluated according to the following criteria.

A: Protective value=100% to 80%
B: Protective value=79% to 50%
C: Protective value=49% to 0%

For the compounds produced in Examples 1, 4, 6, 9, 10, 11, 12, 13, 15, 16, 17, 18, 19, 21, 22, 23, 24, 25, 26, 27, 28, 29, 30, 31, 32, 33, 34, 35, 36, 37, 38, 39, 42, 43, 45, 47, 48, 49, 51, 53, 54, 55, 56, 57, 58, 59, 60, 61, 63, 68, 69, 70, 71, 72, 73, 75, 76, 77, 78, 79, 81, 82, 83, 86, 88, 105, 106, 107, 108, 109, 110, 114, 115, 116, 117, 118, 119, 120, 121, 122, 123, 124, 125, and 126, the protective value was evaluated as A. These compounds had no phytotoxicity.

Test Example 2

Preventive Effect Against Wheat Leaf Rust

The 20% emulsifiable concentrate prepared in Preparation Example 1 was diluted with water to prepare a test solution having a concentration of 200 ppm. The test solution was applied to stems and leaves of fourth-leaf stage wheat seedlings (cultivar: Norin No. 61) raised in an environment controlled greenhouse. The wheat seedlings, to which the test solution had been applied, were air dried. Thereafter, the wheat seedlings were inoculated by spraying with a urediospore suspension of wheat leaf rust fungi (*Puccinia recondita*). The wheat seedlings were then transferred to an environment control room to induce the disease. Fourteen days after the inoculation, the wheat seedlings were compared with those in the nontreated plot to calculate the protective value from the area of the disease. The results were evaluated according to the above criteria.

For the compounds produced in Examples 29, 43, 53, 56, 57, 59, and 63, the protective value was evaluated as A. These compounds had no phytotoxicity.

Test Example 3

Preventive Effect Against Powdery Mildew of Cucumber

The 20% emulsifiable concentrate prepared in Preparation Example 1 was diluted with water to prepare a test solution having a concentration of 200 ppm. The test solution was applied to stems and leaves of cucumber seedlings (cultivar: Suyo) of first leaf development stage raised in a environment controlled greenhouse. The cucumber seedlings, to which the test solution had been applied, were air dried. Thereafter, the cucumber seedlings were inoculated by spraying with a spore suspension of cucumber powdery mildew fungi (*Sphaerotheca fuliginea*) to the leaf face. The cucumber seedlings were then transferred to an environment control room to induce the disease. Ten days after the inoculation, the cucumber seedlings were compared with those in the nontreated plot to calculate the protective value from the area of the disease. The results were evaluated according to the above criteria.

For the compounds produced in Examples 6, 23, 28, 29, 33, 34, 35, 36, 40, 48, 56, 71, 111, and 114, the protective value was evaluated as A. These compounds had no phytotoxicity.

TABLE 1

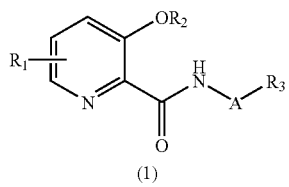

wherein $R_1$ and $R_2$ are H.

| Ex. | A—$R_3$ |
|---|---|
| 1 | |
| 2 | |
| 3 | |
| 4 | |
| 5 | |
| 6 | |
| 7 | |

TABLE 2

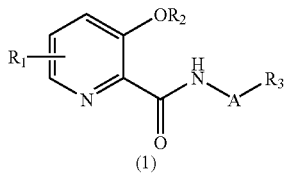

(1)

wherein $R_1$ represents 4-methoxy; and $R_2$ represents a hydrogen atom, provided that $R_2$ represents benzyl for Examples 8 and 131 and represents acetyl for Example 132.

| Ex. | A—R₃ |
|---|---|
| 8 | (4-methylphenyl)–O–phenyl |
| 9 | (4-methylphenyl)–O–phenyl |
| 10 | (4-methylphenyl)–O–(4-tert-butylphenyl) |
| 11 | (3-methylphenyl)–O–phenyl |
| 12 | (2-methylphenyl)–O–phenyl |
| 13 | (4-methylphenyl)–CH₂–phenyl |
| 14 | (4-methylphenyl)–S–phenyl |
| 15 | (4-methylphenyl)–O–(4-methoxyphenyl) |
| 16 | (4-methyl-2-CF₃-phenyl)–O–(4-CF₃-phenyl) |

TABLE 2-continued

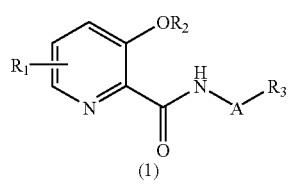

(1)

wherein $R_1$ represents 4-methoxy; and $R_2$ represents a hydrogen atom, provided that $R_2$ represents benzyl for Examples 8 and 131 and represents acetyl for Example 132.

| Ex. | A—R₃ |
|---|---|
| 17 | (4-methylphenyl)–O–(4-biphenyl) |
| 18 | (4-methylphenyl)–O–(4-methylphenyl) |
| 19 | (4-methyl-2-CF₃-phenyl)–O–(4-methylphenyl) |
| 20 | (4-methyl-3-methoxyphenyl)–O–phenyl |
| 21 | (4-methyl-2-chlorophenyl)–O–phenyl |
| 22 | (5-methyl-2-CF₃-phenyl)–O–phenyl |
| 23 | (2,5-dimethylphenyl)–O–phenyl |
| 24 | (4-methyl-3-methoxyphenyl)–O–(4-methylphenyl) |

TABLE 2-continued
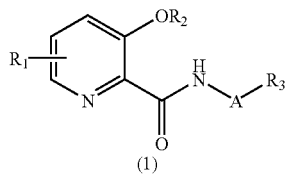
(1)
wherein R₁ represents 4-methoxy; and R₂ represents a hydrogen atom, provided that R₂ represents benzyl for Examples 8 and 131 and represents acetyl for Example 132.
| Ex. | A—R₃ |
|---|---|
| 25 | 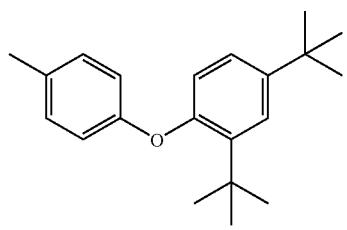 |
| 26 | 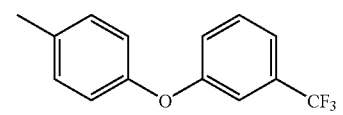 |
| 27 | 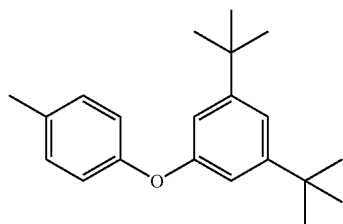 |
| 28 | 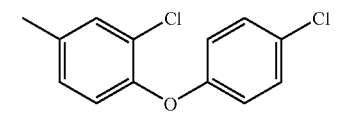 |
| 29 | 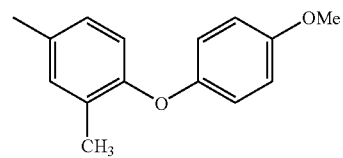 |
| 30 | 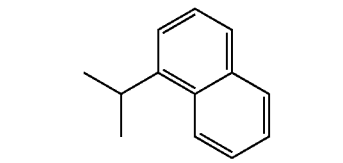 |
| 31 | 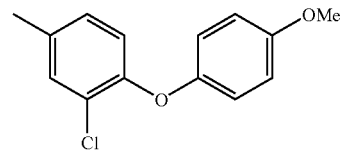 |
TABLE 2-continued
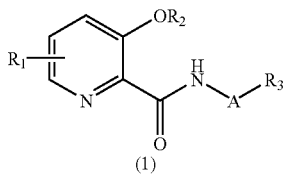
(1)
wherein R₁ represents 4-methoxy; and R₂ represents a hydrogen atom, provided that R₂ represents benzyl for Examples 8 and 131 and represents acetyl for Example 132.
| Ex. | A—R₃ |
|---|---|
| 32 | 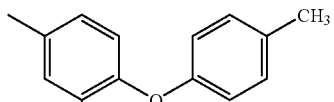 |
| 33 | 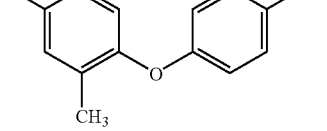 |
| 34 | 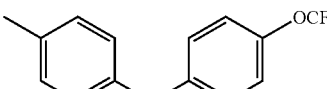 |
| 35 | 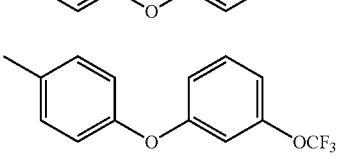 |
| 36 | 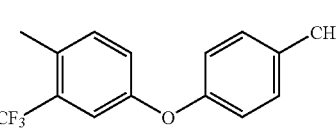 |
| 37 | 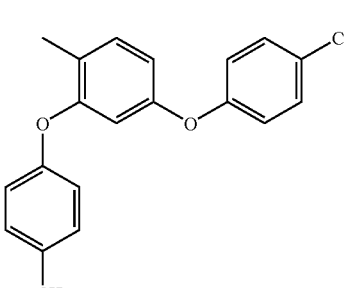 |
| 38 | 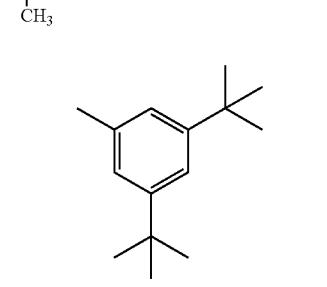 |

TABLE 2-continued
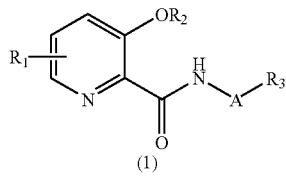
(1)
wherein R₁ represents 4-methoxy; and R₂ represents a hydrogen atom, provided that R₂ represents benzyl for Examples 8 and 131 and represents acetyl for Example 132.
| Ex. | A—R₃ |
|---|---|
| 39 | |
| 40 | |
| 41 | |
| 42 | |
| 43 | |
| 44 | |
| 45 | |
| 46 | |
| 47 | |
| 48 | |
| 49 | |
| 50 | |
| 51 | |
| 52 | |
| 53 | |
| 54 | |
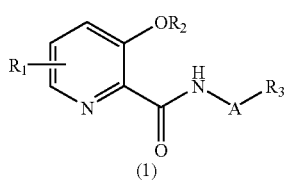

TABLE 2-continued

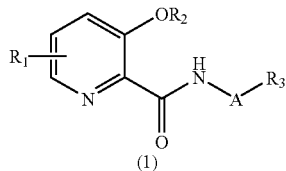

(1)

wherein R₁ represents 4-methoxy; and R₂ represents a hydrogen atom, provided that R₂ represents benzyl for Examples 8 and 131 and represents acetyl for Example 132.

| Ex. | A—R₃ |
|---|---|
| 55 | 3,4-dimethylphenyl phenyl ether |
| 56 | spiro-cyclopropyl-phenylmethyl |
| 57 | methylcycloheptyl |
| 58 | 4-(4-isopropylaminophenoxy)tolyl |
| 59 | methylcyclohexyl |
| 60 | methylphenyl |
| 61 | 4-chloro-methylphenyl |
| 62 | 4-(4-aminophenoxy)tolyl |
| 63 | 2-cyclohexylethyl |
| 64 | 4-benzoyl-methylphenyl |
| 65 | 1-methylindanyl |
| 66 | 1-methyltetrahydronaphthyl |
| 67 | ethylphenyl |
| 68 | propylphenyl |
| 69 | isopropylphenyl |
| 70 | tert-butylphenyl |
| 71 | 4-ethyl-phenoxyphenyl |
| 72 | 4-(2-phenylethoxy)methylphenyl |
| 73 | 4-[4-(isobutyryl)piperazin-1-yl]methylphenyl |

TABLE 2-continued

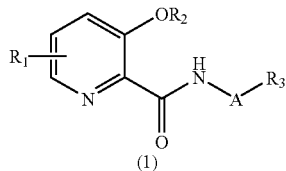

(1)

wherein $R_1$ represents 4-methoxy; and $R_2$ represents a hydrogen atom, provided that $R_2$ represents benzyl for Examples 8 and 131 and represents acetyl for Example 132.

| Ex. | A—R$_3$ |
|---|---|
| 74 | N-methylazepane |
| 75 | ethylcyclohexyl |
| 76 | trans-dimethylcyclohexyl |
| 77 | cis-dimethylcyclohexyl |
| 78 | 1,4-dimethylcyclohexyl |
| 79 | methylcyclopentyl |
| 80 | methylcyclopropyl |
| 81 | methylcyclobutyl |
| 82 | isopentyl |
| 83 | heptyl chain |
| 84 | 4-methylcyclohexanol |
| 85 | 2-methylcyclohexanol |

TABLE 2-continued

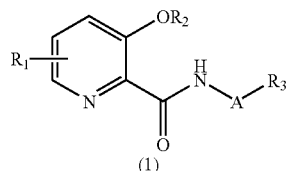

(1)

wherein $R_1$ represents 4-methoxy; and $R_2$ represents a hydrogen atom, provided that $R_2$ represents benzyl for Examples 8 and 131 and represents acetyl for Example 132.

| Ex. | A—R$_3$ |
|---|---|
| 86 | nonyl chain |
| 87 | methyloctyl chain |
| 88 | 2,2-dimethylpentyl |
| 105 | 4-methylphenoxyethoxyphenyl |
| 106 | (R)-isopropylphenyl |
| 107 | (S)-isopropylphenyl |
| 108 | 2,2,4,4-tetramethylpentyl |
| 109 | 4-methylphenoxy propylphenyl |
| 110 | 4-methyl-2-chlorophenoxyethylphenyl |
| 111 | dichlorohexyl |

TABLE 2-continued

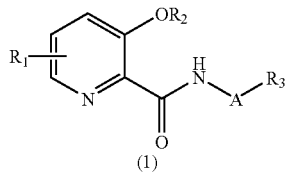

(1)

wherein R₁ represents 4-methoxy; and R₂ represents a hydrogen atom, provided that R₂ represents benzyl for Examples 8 and 131 and represents acetyl for Example 132.

| Ex. | A—R₃ |
|---|---|
| 112 | (4-phenylbutyl) |
| 113 | (5-phenylpentyl) |
| 114 | (4-tert-butylbenzyl) |
| 115 | (4-trifluoromethylbenzyl) |
| 116 | (4-trifluoromethoxybenzyl) |
| 117 | (S)-isopropylcyclohexylmethyl |
| 118 | (R)-isopropylcyclohexylmethyl |
| 119 | 4-(4-chlorophenethoxy)benzyl |
| 120 | (4-fluorobenzyl) |
| 121 | (2-fluoro-4-methylbenzyl) |

TABLE 2-continued

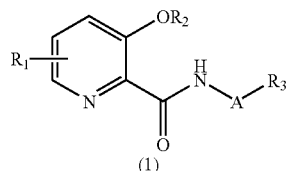

(1)

wherein R₁ represents 4-methoxy; and R₂ represents a hydrogen atom, provided that R₂ represents benzyl for Examples 8 and 131 and represents acetyl for Example 132.

| Ex. | A—R₃ |
|---|---|
| 122 | (3,5-difluorobenzyl) |
| 123 | (4-methylbenzyl) |
| 124 | 4-(3-phenoxypropoxy)benzyl |
| 125 | 4-neopentylbenzyl |
| 126 | (pyridin-2-ylmethyl) |
| 127 | (3,4-dichlorobenzyl) |
| 128 | (2,3-dimethyl-5-tert-butylbenzyl) |
| 129 | (3-chloro-4-tert-butylbenzyl) |
| 130 | (3-methyl-5-tert-butylisoxazol-... ylmethyl) |

TABLE 2-continued

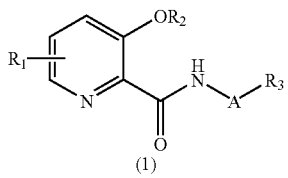
(1)

wherein R₁ represents 4-methoxy; and R₂ represents a hydrogen atom, provided that R₂ represents benzyl for Examples 8 and 131 and represents acetyl for Example 132.

| Ex. | A—R₃ |
|---|---|
| 131 | 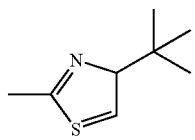 |
| 132 | 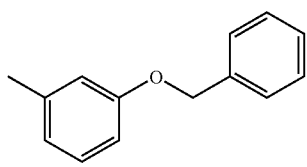 |

TABLE 3

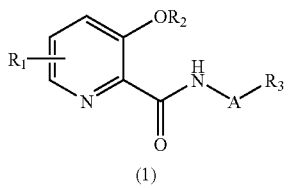
(1)

wherein R₁ represents 6-methoxy; and R₂ represents a hydrogen atom, provided that R₂ represents benzyl only for Example 89.

| Ex. | A—R₃ |
|---|---|
| 89 | 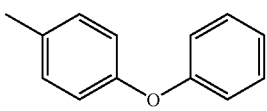 |
| 90 | 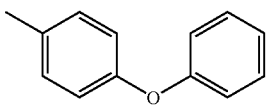 |
| 91 | 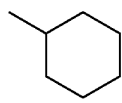 |

TABLE 4

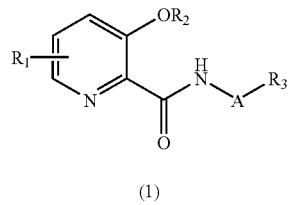
(1)

wherein R₁ represents dimethoxy; and R₂ represents a hydrogen atom.

| Ex. | Compound |
|---|---|
| 92 | 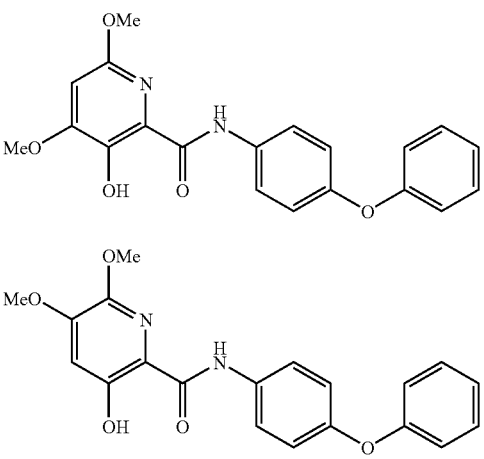 |
| 93 | |

TABLE 5

| Comp. No. | $^1$H-NMR δ (ppm) | Solvent for measurement |
|---|---|---|
| 1 | 6.94–7.06(m, 5H), 7.25–7.35(m, 4H), 7.59–7.63(m, 2H), 8.06(dd, 1H), 9.82 (s, 1H), 11.86(s, 1H) | c |
| 2 | 3.97(s, 2H), 7.17–7.22(m, 5H), 7.26–7.39 (m, 4H), 7.61(m, 2H), 8.10(dd, 1H), 9.85 (s, 1H), 11.94(s, 1H) | c |
| 3 | 0.72–0.82(m, 6H), 1.16–1.23(m, 6H), 1.50–1.56(m, 4H), 2.77–2.81(m, 2H), 6.78–7.37(m, 7H), 7.55–7.61(m, 2H), 8.09(dd, 1H), 9.81(s, 1H), 11.97(s, 1H) | c |
| 4 | 1.32(s, 9H), 6.95(d, 2H), 7.05(d, 2H), 7.35(d, 2H), 7.36(dd, 1H), 7.40(dd, 1H), 7.66(d, 2H), 8.13(dd, 1H), 9.88(br, 1H), 11.95(s, 1H) | c |
| 5 | 1.33(s, 9H), 1.42(s, 9H), 6.76(d, 1H), 7.02(d, 2H), 7.14(dd, 1H), 7.36(dd, 1H), 7.40(dd, 1H), 7.41(d, 1H), 7.64(d, 2H), 8.13(dd, 1H), 9.86(br, 1H), 11.98(s, 1H) | c |
| 6 | 7.09(d, 2H), 7.17(d, 1H), 7.37(dd, 1H), 7.30–7.46(m, 3H), 7.42(dd, 1H), 7.73(d, 2H), 8.13(dd, 1H), 9.94(br, 1H), 11.88(s, 1H) | c |
| 7 | 1.23–1.49(m, 5H), 1.64(m, 1H), 1.79(m, 2H), 2.02(m, 2H), 3.92(m, 1H), 7.29 (dd, 1H), 7.33 (dd, 1H), 7.93(br, 1H), 8.04(dd, 1H), 12.33 (s, 1H) | c |
| 8 | 4.01(s, 3H), 5.05(s, 2H), 6.93–7.12(m, 6H), 7.27–7.48(m, 7H), 7.74–7.78(m, 2H), 8.31 (d, 1H), 10.46(s, 1H) | d |
| 9 | 3.96(s, 3H), 6.89–7.10(m, 6H), 7.24–7.34 (m, 2H), 7.64–7.67(m, 2H), 8.01(d, 1H), 9.90(s, 1H), 12.17(s, 1H) | c |
| 10 | 1.33(s, 9H), 3.98(s, 3H), 6.91(d, 1H), 6.95 (d, 2H), 7.02(d, 2H), 7.35(d, 2H), 7.65 (d, 2H), 8.03(d, 1H), 9.91(br, 1H), 12.20 (s, 1H) | c |

TABLE 5-continued

| Comp. No. | ¹H-NMR δ (ppm) | Solvent for measurement |
|---|---|---|
| 11 | 3.90(s, 3H), 6.75–7.08(m, 5H), 7.25–7.45 (m, 5H), 7.94(d, 1H), 9.87(s, 1H), 12.01 (s, 1H) | c |
| 12 | 3.89(s, 3H), 6.80–7.12(m, 7H), 7.29–7.33 (m, 2H), 7.91(d, 1H), 8.48(d, 1H), 10.51 (s, 1H), 12.09(s, 1H) | c |
| 13 | 3.95(s, 3H), 3.97(s, 2H), 6.89(d, 1H), 7.16–7.29 (m, 7H), 7.60(d, 2H), 8.00(d, 1H), 9.88(s, 1H), 12.20(s, 1H) | c |
| 14 | 3.96(s, 3H), 6.94(d, 1H), 7.18–7.30(m, 5H), 7.40(d, 2H), 7.66(d, 2H), 8.01(d, 1H), 9.97 (s, 1H), 12.05(s, 1H) | c |
| 15 | 3.79(s, 3H), 3.95(s, 3H), 6.86–6.98(m, 7H), 7.61(d, 2H), 8.00(d, 1H), 9.87(s, 1H), 12.19 (s, 1H) | c |
| 16 | 3.97(s, 3H), 6.92(d, 1H), 7.04–7.07(m, 3H), 7.59(d, 2H), 7.92(m, 1H), 8.03(d, 1H), 8.06 (d, 1H), 10.08(s, 1H), 11.85(s, 1H) | c |
| 17 | 3.96(s, 3H), 6.90(d, 1H), 7.04–7.10(m, 4H), 7.29–7.35(m, 1H), 7.40–7.43(m, 2H), 7.50–7.56(m, 4H), 7.67–7.69 (m, 2H), 8.01(d, 1H), 9.92(s, 1H), 12.17 (s, 1H) | c |
| 18 | 2.34(s, 3H), 3.98(s, 3H), 6.91(d, 1H), 6.92 (d, 2H), 7.02(d, 2H), 7.12(d, 2H), 7.65 (d, 2H), 8.03(d, 1H), 9.90(br, 1H), 12.20 (s, 1H) | c |
| 19 | 2.35(s, 3H), 3.98(s, 3H), 6.92–6.98(m, 4H), 7.17(d, 2H), 7.81(dd, 1H), 8.01(d, 1H), 8.04(d, 1H), 10.00(br, 1H), 11.96(s, 1H) | c |
| 20 | 3.92(s, 3H), 3.97(s, 3H), 6.64(dd, 1H), 6.69(d, 1H), 6.91(d, 1H), 7.02(dd, 2H), 7.11(m, 1H), 7.34(dd, 2H), 8.07(d, 1H), 8.38(d, 1H), 10.38(br, 1H), 12.30(s, 1H) | c |
| 21 | 3.98(s, 3H), 6.91–7.29(m, 5H), 7.33(m, 2H), 7.53(m, 1H), 7.97(d, 1H), 8.03(d, 1H), 9.97 (br, 1H), 11.99(s, 1H) | c |
| 22 | 3.98(s, 3H), 6.93(d, 1H), 6.99(d, 1H), 7.04 (dd, 2H), 7.16(t, 1H), 7.37(dd, 2H)7.84 (dd, 1H), 8.03(d, 1H), 8.04(d, 1H), 10.02 (br, 1H), 11.94(s, 1H) | c |
| 23 | 2.27(s, 3H), 3.98(s, 3H), 6.91(m, 1H), 6.91 (dd, 2H), 6.95(d, 1H), 7.05(t, 1H), 7.31 (dd, 2H), 7.49(dd, 1H), 7.64(d, 1H), 8.03 (d, 1H), 9.91(br, 1H), 12.21(s, 1H) | c |
| 24 | 2.34(s, 3H), 3.91(s, 3H), 3.97(s, 3H), 6.60 (dd, 1H), 6.66(d, 1H), 6.90(d, 1H), 6.92(d, 2H), 7.14(d, 2H), 8.06(d, 1H), 8.34(d, 1H), 10.36 (br, 1H), 12.31(s, 1H) | c |
| 25 | 1.32(s, 9H), 1.42(s, 9H), 3.98(s, 3H), 6.75 (d, 1H), 6.91(d, 1H), 7.01(d, 2H), 7.14(dd, 1H), 7.41(d, 1H), 7.64(d, 2H), 8.03(d, 1H), 9.89 (br, 1H), 12.23(s, 1H) | c |
| 26 | 3.98(s, 3H), 6.93(d, 1H), 7.08(d, 2H), 7.16 (d, 1H), 7.26(s, 1H), 7.34(d, 1H), 7.43(dd, 1H), 7.73(d, 2H), 8.04(d, 1H), 9.97(br, 1H), 12.13 (s, 1H) | c |
| 27 | 1.30(s, 18H), 3.98(s, 3H), 6.88(d, 2H), 6.91 (d, 1H), 7.04(d, 2H), 7.18(t, 1H), 7.66(d, 2H), 8.03(d, 1H), 9.92(br, 1H), 12.22(s, 1H) | c |
| 28 | 3.98(s, 3H), 6.89(d, 2H), 6.93(d, 1H), 7.04 (d, 1H), 7.28(d, 2H), 7.55(dd, 1H), 7.97(d, 1H), 8.03(d, 1H), 9.98(br, 1H), 11.95(s, 1H) | c |
| 29 | 2.28(s, 3H), 3.78(s, 3H), 3.95(s, 3H), 6.80–6.90 (m, 6H), 7.41(dd, 1H), 7.59(d, 1H), 8.00 (d, 1H), 9.85(s, 1H), 12.21(s, 1H) | c |
| 30 | 1.77(d, 3H), 3.92(s, 3H), 6.05(t, 1H), 6.83 (d, 1H), 7.44–7.59(m, 4H), 7.80(d, 1H), 7.86 (d, 1H), 7.89(d, 1H), 8.14(d, 1H), 8.33(br, 1H), 12.41(s, 1H) | c |
| 31 | 3.79(s, 3H), 3.96(s, 3H), 6.85–6.98(m, 6H), 7.45(dd, 1H), 7.91(d, 1H), 8.00(d, 1H), 9.91 (br, 1H), 11.99(s, 1H) | c |
| 32 | 2.33(s, 3H), 3.98(s, 3H), 6.88(d, 2H), 6.92 (d, 1H), 6.98(d, 1H), 7.14(d, 2H), 7.50(dd, 1H), 7.95(d, 1H), 8.03(d, 1H), 9.95(br, 1H), 12.01 (s, 1H) | c |
| 33 | 2.28(s, 3H), 2.32(s, 3H), 3.98(s, 3H), 6.82 (d, 2H), 6.91(d, 1H), 6.92(d, 1H), 7.11(d, 2H), 7.46(dd, 1H), 7.62(d, 1H), 8.03(d, 1H), 9.89 (br, 1H), 12.22(s, 1H) | c |
| 34 | 3.98(s, 3H), 6.92(d, 1H), 7.01(d, 2H), 7.06 (d, 2H), 7.09(d, 2H), 7.71(d, 2H), 8.04(d, 1H), 9.95(br, 1H), 12.14(s, 1H) | c |
| 35 | 3.98(s, 3H), 6.86(m, 1H), 6.93(d, 1H), 6.90–6.96(m, 2H), 7.09(d, 2H), 7.33(dd, 1H), 7.73(d, 2H), 8.04(d, 1H), 9.97(br, 1H), 12.14 (s, 1H) | c |
| 36 | 2.36(s, 3H), 3.98(s, 3H), 6.93(d, 1H), 6.94 (d, 1H), 7.18(d, 2H), 7.19(dd, 1H), 7.30(d, 1H), 8.07(d, 1H), 8.23(d, 1H), 10.37(br, 1H), 11.85 (s, 1H) | c |
| 37 | 2.31(s, 3H), 2.34(s, 3H), 3.96(s, 3H), 6.57 (d, 1H), 6.70(dd, 1H), 6.87(d, 2H), 6.88(d, 1H), 7.01(d, 2H), 7.10(d, 2H), 7.16(d, 2H), 7.99 (d, 1H), 8.42(d, 1H), 10.47(br, 1H), 12.20 (s, 1H) | c |
| 38 | 1.36(s, 18H), 3.98(s, 3H), 6.91(d, 1H), 7.25 (d, 1H), 7.56(d, 2H), 8.04(d, 1H), 9.91(br, 1H), 12.33(s, 1H) | c |
| 39 | 3.95(s, 3H), 5.06(s, 2H), 6.89(d, 1H), 6.97–7.00 (m, 2H), 7.29–7.43(m, 5H), 7.60(d, 2H), 8.00 (d, 1H), 9.82(s, 1H), 12.25(s, 1H) | c |
| 40 | 3.95(s, 3H), 5.09(s, 2H), 6.79(d, 1H), 6.89 (d, 1H), 7.17–7.45(m, 7H), 8.01(d, 1H), 9.93 (br, 1H), 12.15(s, 1H) | c |
| 41 | 3.97(s, 3H), 6.92(d, 1H), 7.36–7.40(m, 2H), 7.49(dd, 1H), 7.71(d, 1H), 7.91(m, 1H), 7.99–8.04(m, 2H), 8.60(m, 1H), 8.87(d, 1H), 10.06(s, 1H), 12.08(s, 1H) | c |
| 42 | 1.36–1.70(m, 20H), 1.73(m, 2H), 3.92(s, 3H), 4.18(m, 1H), 6.83(d, 1H), 7.85(br, 1H), 7.92 (dd, 1H), 12.59(s, 1H) | c |
| 43 | 1.45–1.72(m, 12H), 1.91(m, 2H), 3.92(s, 3H), 4.12(m, 1H), 6.83(d, 1H), 7.92(dd, 1H), 7.97 (br, 1H), 12.60(s, 1H) | c |
| 44 | 3.90(s, 3H), 5.64(br, 1H), 6.86(m, 2H), 6.99 (d, 2H), 7.04(d, 2H), 7.19(m, 1H), 7.54(d, 2H), 7.96(dd,1H), 9.79(br, 1H), 12.23(s, 1H) | c |
| 45 | 1.71(m, 6H), 2.12(m, 9H), 3.91(s, 3H), 6.82 (d, 1H), 7.87(br, 1H), 7.90(dd, 1H), 12.69(s, 1H) | c |
| 46 | 3.14(m, 4H), 3.85(m, 4H), 3.95(s, 3H), 6.88 (d, 1H), 6.92(d, 2H), 7.59(d, 2H), 8.00(d, 1H), 9.80(br, 1H), 12.29(s, 1H) | c |
| 47 | 1.53(m, 6H), 1.67(m, 6H), 1.98(m, 3H), 3.11 (d, 2H), 3.93(s, 3H), 6.84(d, 1H), 7.95(d, 1H), 8.13(br, 1H), 12.55(s, 1H) | c |
| 48 | 2.25(s, 3H), 3.98(s, 3H), 6.93(d, 1H), 6.98 (d, 1H), 7.05(d, 1H), 7.16(m, 1H), 7.28(d, 1H), 7.40(dd, 1H), 7.53(dd, 1H), 7.68(d, 1H), 8.04 (d, 1H), 9.95(br, 1H), 12.15(s, 1H) | c |
| 49 | 1.23–1.28(m, 1H), 1.36–1.44(m, 2H), 1.73–1.78 (m, 1H), 1.81–1.91(m, 5H), 3.97(s, 3H), 6.91 (d, 1H), 7.24(d, 2H), 7.61(d, 2H), 8.03(d, 1H), 9.89(br, 1H), 12.28(s, 1H) | c |
| 50 | 3.75(m, 8H), 3.90(m, 4H), 3.95(s, 3H), 4.15 (m, 4H), 6.87(m, 2H), 7.09(dd, 1H), 7.43(d, 1H), 7.99(d, 1H), 9.83(br, 1H), 12.20(s, 1H) | c |
| 51 | 3.95(s, 3H), 4.25(m, 4H), 6.85(d, 1H), 6.88 (d, 1H), 7.08(dd, 1H), 7.32(m, 1H), 7.99(dd, 1H), 9.77(br, 1H), 12.23(s, 1H) | c |
| 52 | 1.63(m, 2H), 1.98(m, 2H), 2.17(m, 2H), 2.84 (m, 2H), 3.50(s, 2H), 3.92(s, 3H), 3.92(m, 1H), 6.84(d, 1H), 7.24(m, 1H), 7.30(m, 4H), 7.93 (dd, 1H), 7.93(br, 1H), 12.47(s, 1H) | c |
| 53 | 1.53(m, 2H), 1.63(m, 2H), 1.97(m, 4H), 2.23 (t, 2H), 3.49(m, 2H), 3.92(s, 3H), 5.51(s, 1H), 6.83(d, 1H), 7.92(dd, 1H), 8.01(br, 1H), 12.52 (s, 1H) | c |

TABLE 5-continued

| Comp. No. | ¹H-NMR δ (ppm) | Solvent for measurement |
|---|---|---|
| 54 | 3.99(s, 3H), 6.94(d, 1H), 7.04(d, 2H), 7.14 (d, 2H), 7.79(d, 2H), 8.05(d, 1H), 8.22(d, 2H), 10.02(br, 1H), 12.06(s, 1H) | c |
| 55 | 2.26(s, 6H), 3.98(s, 3H), 6.78(s, 2H), 6.93 (d, 1H), 7.04(d, 2H), 7.11(t, 1H), 7.35(t, 2H), 8.05(d, 1H), 9.34(br, 1H), 12.27(s, 1H) | c |
| 56 | 1.32–1.40(m, 2H), 2.21–2.25(m, 1H), 3.06–3.11 (m, 1H), 3.94(s, 3H), 6.87(d, 1H), 7.18–7.22 (m, 3H), 7.30(t, 2H), 7.95(d, 1H), 8.19(br, 1H), 12.36(s, 1H) | c |
| 57 | 1.45–1.70(m, 10H), 2.00(m, 2H), 3.92(s, 3H), 4.08(m, 1H), 6.83(d, 1H), 7.93(dd, 1H), 7.96 (br, 1H), 12.60(s, 1H) | c |
| 58 | 1.22(d, 6H), 3.59(m, 1H), 3.97(s, 3H), 6.58 (d, 2H), 6.89(d, 2H), 6.91(d, 1H), 6.96(d, 2H), 7.60(d, 2H), 8.02(d, 1H), 9.86(br, 1H), 12.24 (s, 1H) | c |
| 59 | 1.17–1.51(m, 5H), 1.64(m, 1H), 1.77(m, 2H), 1.98(m, 2H), 3.89(m, 1H), 3.92(s, 3H), 6.83 (d, 1H), 7.92(br, 1H), 7.93(dd, 1H), 12.60(s, 1H) | c |
| 60 | 3.98(s, 3H), 6.92(d, 1H), 7.19(t, 1H), 7.40(t, 2H), 7.72(d, 2H), 8.04(d, 1H), 9.96(br, 1H), 12.20 (s, 1H) | c |
| 61 | 3.98(s, 3H), 6.93(d, 1H), 7.36(d, 2H), 7.68 (d, 2H), 8.03(d, 1H), 9.97(br, 1H), 12.04 (s, 1H) | c |
| 62 | 3.97(s, 3H), 6.69(d, 2H), 6.88(d, 2H), 6.91 (d, 1H), 6.97(d, 2H), 7.61(d, 2H), 8.02(d, 1H), 9.87(br, 1H), 12.23(s, 1H) | c |
| 63 | 0.89(m, 2H), 1.13(m, 1H), 1.30(m, 1H), 1.45 (m, 4H), 1.64(m, 4H), 3.39(m, 2H), 3.88(s, 3H), 6.79(d, 1H), 7.88(d, 1H), 7.92(br, 1H), 12.49 (s, 1H) | c |
| 64 | 3.92(s, 3H), 6.88(d, 1H), 7.43(t, 1H), 7.53 (m, 1H), 7.73(m, 2H), 7.78(m, 2H), 7.83(m, 1H), 7.99(d, 1H), 10.13(br, 1H), 11.87(s, 1H) | c |
| 65 | 1.96–2.05(m, 1H), 2.64–2.72(m, 1H), 2.91–2.99 (m, 1H), 3.04–3.12(m, 1H), 3.96(s, 3H), 5.60–5.66(m, 1H), 6.86(d, 1H), 7.22–7.28(m, 3H), 7.36(d, 1H), 7.92(d, 1H), 8.24(br, 1H), 12.49 (s, 1H) | c |
| 66 | 1.88–2.00(m, 3H), 2.13–2.20(m, 1H), 2.79–2.91 (m, 2H), 3.95(s, 3H), 5.30–5.36(m, 1H), 6.85 (d, 1H), 7.13–7.22(m, 3H), 7.31(d, 1H), 7.91 (d, 1H), 8.29(br, 1H), 12.53(s, 1H) | c |
| 67 | 3.95(s, 3H), 4.64(d, 2H), 6.86(d, 1H), 7.28–7.38 (m, 5H), 7.94(d, 1H), 8.36(br, 1H), 12.38(s, 1H) | c |
| 68 | 2.95(t, 2H), 3.70(q, 2H), 3.94(s, 3H), 6.85 (d, 1H), 7.23–7.26(m, 3H), 7.31–7.34 (m, 2H), 7.92(d, 1H), 8.12(br, 1H), 12.44(s, 1H) | c |
| 69 | 1.63(d, 3H), 3.94(s, 3H), 5.25(qu, 1H), 6.86 (d, 1H), 7.28(m, 1H), 7.34–7.41(m, 4H), 7.95 (d, 1H), 8.31(br, 1H), 12.38(s, 1H) | c |
| 70 | 1.83(s, 6H), 3.93(s, 3H), 6.86(d, 1H), 7.26(t, 1H), 7.35(t, 2H), 7.45(d, 2H), 7.96(d, 1H), 8.48 (br, 1H), 12.35(s, 1H) | c |
| 71 | 3.95(s, 3H), 4.60(d, 2H), 6.87(d, 1H), 6.97–7.02 (m, 4H), 7.10(t, 1H), 7.31–7.35(m, 4H), 7.95 (d, 1H), 8.34(br, 1H), 12.37(s, 1H) | c |
| 72 | 3.11(t, 2H), 3.97(s, 3H), 4.19(t, 2H), 6.90(d, 1H), 6.92(d, 2H), 7.23–7.35(m, 5H), 7.60(d, 2H), 8.02 (d, 1H), 9.83(br, 1H), 12.27(s, 1H) | c |
| 73 | 1.16(d, 6H), 2.84(m, 1H), 3.16(br, 4H), 3.69 (br, 2H), 3.80(br, 2H), 3.97(s, 3H), 6.90 (d, 1H), 6.96(d, 2H), 7.62(d, 2H), 8.02(d, 1H), 9.84(br, 1H), 12.28(s, 1H) | c |
| 74 | 1.61(m, 4H), 1.72(m, 4H), 3.06(t, 4H), 3.87 (s, 3H), 6.79(d, 1H), 7.86(d, 1H), 8.94(br, 1H), 12.30(s, 1H) | c |
| 75 | 0.97–1.07(m, 2H), 1.13–1.30(m, 3H), 1.55–1.64 (m, 1H), 1.66–1.69(m, 1H), 1.73–1.81(m, 4H), 3.28(t, 2H), 3.94(s, 3H), 6.86(d, 1H), 7.95 (d, 1H), 8.11(br, 1H), 12.55(s, 1H) | c |
| 76 | 0.97(d, 3H), 1.13–1.19(m, 1H), 1.23–1.33 (m, 2H), 1.35–1.44(m, 2H), 1.69–1.73(m, 1H), 1.78–1.84(m, 2H), 2.01–2.05(m, 1H), 3.58–3.62 (m, 1H), 3.94(s, 3H), 6.86(d, 1H), 7.86(br, 1H), 7.95(d, 1H), 12.64(s, 1H) | c |
| 77 | 0.94(d, 3H), 1.34–1.43(m, 2H), 1.53–1.70 (m, 5H), 1.77–1.83(m, 1H), 1.90–1.96(m, 1H), 3.94(s, 3H), 4.17–4.22(m, 1H), 6.86(d, 1H), 7.96 (d, 1H), 8.21(br, 1H), 12.61(s, 1H) | c |
| 78 | 0.92(d, 3H), 0.97(d, 3H), 1.05–1.16(m, 2H), 1.25–1.40(m, 6H), 1.58(m, 1H), 1.63–1.83 (m, 8H), 2.02–2.08(m, 1H), 3.80–3.88(m, 1H), 3.94(s, 3H), 3.95(s, 3H), 4.12–4.17(m, 1H), 6.85(d, 1H), 6.86(d, 1H), 7.87(br, 1H), 7.94 (d, 1H), 7.97(d, 1H), 8.20(br, 1H), 12.60(s, 1H), 12.61(br, 1H) | c |
| 79 | 1.59–1.62(m, 2H), 1.64–1.72(m, 2H), 1.76–1.79 (m, 2H), 2.04–2.10(m, 2H), 3.94(s, 3H), 4.33–4.40(m, 1H), 6.85(d, 1H), 7.94(d, 1H), 7.94 (br, 1H), 12.59(s, 1H) | c |
| 80 | 0.70(m, 2H), 0.89(m, 2H), 2.90(m, 1H), 3.94 (s, 3H), 6.86(d, 1H), 7.93(d, 1H), 8.03(br, 1H), 12.42(s, 1H) | c |
| 81 | 1.77–1.80(m, 2H), 2.02–2.12(m, 2H), 2.39–2.46 (m, 2H), 3.94(s, 3H), 4.53(m, 1H), 6.86(d, 1H), 7.95(d, 1H), 8.14(br, 1H), 12.47(s, 1H) | c |
| 82 | 0.97(t, 3H), 1.26(d, 3H), 1.61(qu, 2H), 3.94 (s, 3H), 4.00–4.12(m, 1H), 6.86(d, 1H), 7.86 (br, 1H), 7.95(d, 1H), 12.61(s, 1H) | c |
| 83 | 0.89(t, 3H), 1.30–1.34(m, 4H), 1.36–1.42 (m, 2H), 1.59–1.67(m, 2H), 3.43(qu, 2H), 3.94(s, 3H), 6.86(d, 1H), 7.95(d, 1H), 8.04(br, 1H), 12.55(s, 1H) | c |
| 84 | 1.39–1.52(m, 4H), 2.04–2.12(m, 4H), 3.68 (m, 1H), 3.91(m, 1H), 3.94(s, 3H), 6.86(d, 1H), 7.89(br, 1H), 7.94(d, 1H), 12.49(s, 1H) | c |
| 85 | 1.28–1.46(m, 4H), 1.79(m, 2H), 2.11(m, 2H), 3.51(m, 1H), 3.80(m, 1H), 3.95(s, 3H), 6.87 (d, 1H), 7.96(d, 1H), 8.05(br, 1H), 12.26(s, 1H) | c |
| 86 | 0.88(t, 3H), 1.26–1.42(m, 10H), 1.64(m, 2H), 3.43(m, 2H), 3.94(s, 3H), 6.86(d, 1H), 7.95 (d, 1H), 8.03(br, 1H), 12.55(s, 1H) | c |
| 87 | 0.88(t, 3H), 1.25–1.44(m, 8H), 3.43(m, 2H), 3.94(m, 2H), 3.94(s, 3H), 6.86(d, 1H), 7.95 (d, 1H), 8.03(br, 1H), 12.54(s, 1H) | c |
| 88 | 0.98(s, 9H), 1.56(t, 2H), 3.43–3.48(m, 2H), 3.94 (s, 3H), 6.85(d, 1H), 7.94(d, 1H), 7.98(br, 1H), 12.53(s, 1H) | c |
| 89 | 3.52(s, 3H), 4.95(s, 2H), 6.53(d, 1H), 6.98–7.01 (m, 4H), 7.08–7.12(m, 1H), 7.26–7.35(m, 8H), 7.47–7.50(m, 2H), 8.31(br, 1H) | c |
| 90 | 3.57(s, 3H), 6.60(d, 1H), 6.95–7.02(m, 4H), 7.08–7.12(m, 1H), 7.31–7.40(m, 3H), 7.65–7.69(m, 2H) | m |
| 91 | 1.12–1.48(m, 5H), 1.68–2.17(m, 5H), 3.55(s, 3H), 3.94(m, 1H), 6.57(d, 1H), 7.16(d, 1H) | c |
| 94 | 4.05(s, 3H), 5.15(s, 2H), 7.28–7.37(m, 4H), 7.47–7.50(m, 2H), 8.25(d, 1H) | m |
| 95 | 4.03(s, 3H), 7.39(d, 1H), 8.04(d, 1H) | d |
| 96 | 4.14(s, 3H), 7.46(d, 1H), 8.08(d, 1H) | m |
| 97 | 3.44(s, 3H), 3.90(s, 3H), 4.93(s, 2H), 6.60 (d, 1H), 7.25(d, 1H), 7.30~7.44(m, 5H) | c |
| 98 | 3.51(s, 3H), 5.04(s, 2H), 6.52(d, 1H), 7.40~7.45 (m, 5H), 7.61(d, 1H) | w |
| 100 | 3.37(s, 3H), 6.41(d, 1H), 7.21(d, 1H) | w |
| 101 | 3.80(s, 3H), 3.81(s, 3H), 3.85(s, 3H), 4.92(s, 2H), 6.27(s, 1H), 7.19~7.39(m, 5H) | c |
| 103 | 3.91(s, 3H), 4.00(s, 3H), 4.01(s, 3H), 5.11(s, 2H), 7.19~7.42(m, 5H), 8.14(s, 1H) | c |
| 105 | 3.95(s, 3H), 4.35(s, 4H), 6.89(d, 1H), 6.96 (m, 5H), 7.28(m, 2H), 7.61(m, 2H), 8.00(d, 1H), 9.84(br, 1H), 12.24(s, 1H) | c |
| 106 | 1.61(d, 3H), 3.92(s, 3H), 5.23(q, 1H), 6.84 (d, 1H), 7.27(m, 1H), 7.36(m, 4H), 7.93(d, 1H), 8.28(br, 1H), 12.36(s, 1H) | c |
| 107 | 1.61(d, 3H), 3.92(s, 3H), 5.23(q, 1H), 6.84 (d, 1H), 7.27(m, 1H), 7.35(m, 4H), 7.93(d, 1H), 8.28(br, 1H), 12.36(s, 1H) | c |

TABLE 5-continued

| Comp. No. | $^1$H-NMR δ (ppm) | Solvent for measurement |
|---|---|---|
| 108 | 1.01(s, 9H), 1.52(s, 6H), 1.83(s, 2H), 3.91(s, 3H), 6.81(d, 1H), 7.90(d, 1H), 8.07(br, 1H), 12.72 (s, 1H) | c |
| 109 | 2.04(m, 2H), 2.75(t, 2H), 3.90(s, 3H), 3.91 (t, 2H), 6.83–6.86(m, 3H), 7.13–7.24 (m, 5H), 7.53(d, 2H), 7.95(d, 1H), 9.76 (br, 1H), 12.21(s, 1H) | c |
| 110 | 3.14(t, 2H), 3.95(s, 3H), 4.21(t, 2H), 6.88 (m, 2H), 7.21–7.31(m, 5H), 7.50(m, 1H), 7.78(d, 1H), 7.99(d, 1H), 9.82(br, 1H), 12.06(s, 1H) | c |
| 111 | 1.99(m, 2H), 2.09(m, 2H), 3.60(t, 2H), 3.90 (m, 1H), 3.95(s, 3H), 4.12(m, 2H), 6.88 (d, 1H), 7.99(d, 1H), 8.44(br, 1H), 12.16 (s, 1H) | c |
| 112 | 1.97(m, 2H), 2.71(t, 2H), 3.46(m, 2H), 3.93 (s, 3H), 6.84(d, 1H), 7.16–7.29(m, 5H), 7.93(d, 1H), 8.05(br, 1H), 12.46(s, 1H) | c |
| 113 | 1.62–1.76(m, 4H), 2.65(t, 2H), 3.44 (m, 2H), 3.92(s, 3H), 6.83(d, 1H), 7.15–7.18 (m, 3H), 7.25–7.28(m, 2H), 7.92(d, 1H), 8.01(br, 1H), 12.48(s, 1H) | c |
| 114 | 1.31(s, 9H), 3.95(s, 3H), 6.89(d, 1H), 7.40 (m, 2H), 7.60(m, 2H), 8.01(d, 1H), 9.87(br, 1H), 12.26(s, 1H) | c |
| 115 | 3.97(s, 3H), 6.92(d, 1H), 7.64(d, 2H), 7.83 (d, 2H), 8.03(d, 1H), 10.12(br, 1H), 11.89 (s, 1H) | c |
| 116 | 3.96(s, 3H), 6.91(d, 1H), 7.24(d, 2H), 7.73 (d, 2H), 8.01(d, 1H), 9.99(br, 1H), 11.99 (s, 1H) | c |
| 117 | 1.00–1.30(m, 5H), 1.25(d, 3H), 1.42–1.50 (m, 1H), 1.63–1.83(m, 5H), 3.94(s, 3H), 3.94–4.03(m, 1H), 6.86(d, 1H), 7.92(br, 1H), 7.95 (d, 1H), 12.63(s, 1H) | c |
| 118 | 1.00–1.28(m, 5H), 1.23(d, 3H), 1.43–1.48 (m, 1H), 1.65–1.83(m, 5H), 3.94(s, 3H), 3.94–4.03(m, 1H), 6.87(d, 1H), 7.94(br, 1H), 7.95 (d, 1H), 12.64(s, 1H) | c |
| 119 | 3.05(t, 2H), 3.95(s, 3H), 4.14(t, 2H), 6.88–6.92 (m, 3H), 7.19–7.31(m, 4H), 7.58(d, 2H), 8.00 (d, 1H), 9.82(br, 1H), 12.24(s, 1H) | c |
| 120 | 3.94(s, 3H), 6.92(d, 1H), 7.10(m, 2H), 7.68 (m, 2H), 8.03(d, 1H), 9.94(br, 1H), 12.11(s, 1H) | c |
| 121 | 2.35(s, 3H), 3.97(s, 3H), 6.92(d, 1H), 6.97–7.00 (m, 2H), 8.05(d, 1H), 8.25(m, 1H), 10.16 (br, 1H), 12.04(s, 1H), | c |
| 122 | 3.96(s, 3H), 6.61(m, 1H), 6.91(d, 1H), 7.32 (m, 2H), 8.01(d, 1H), 10.04(br, 1H), 11.79 (s, 1H) | c |
| 123 | 2.33(s, 3H), 3.95(s, 3H), 6.89(d, 1H), 7.18 (d, 2H), 7.57(d, 2H), 8.01(d, 1H), 9.87 (br, 1H), 12.25(s, 1H) | c |
| 124 | 2.25(m, 2H), 3.95(s, 3H), 4.11–4.17(m, 4H), 6.88–6.94(m, 6H), 7.24–7.28(m,2H), 7.57–7.60 (m, 2H), 8.00(d, 1H), 9.82(br, 1H), 12.26(s, 1H) | c |
| 125 | 0.89(s, 9H), 2.47(s, 2H), 3.95(s, 3H), 6.89 (d, 1H), 7.13(d, 2H), 7.58(d, 2H), 8.01(d, 1H), 9.89(br, 1H), 12.25(s, 1H) | c |
| 126 | 3.98(s, 3H), 6.93(d, 1H), 7.11(m, 1H), 7.78 (m, 1H), 8.06(d, 1H), 8.31(m, 1H), 8.39(m, 1H), 10.48(br, 1H), 11.94(s, 1H) | c |
| 127 | 3.96(s, 3H), 6.92(d, 1H), 7.33(m, 1H), 7.50 (m, 1H), 7.69(m, 1H), 8.01(d, 1H), 10.02 (br, 1H), 12.04(s, 1H) | c |
| 128 | 1.31(s, 9H), 2.29(s, 6H), 4.14(s, 3H), 6.92 (d, 1H), 7.14(s, 2H), 8.03(d, 1H), 9.35 (br, 1H), 12.37(s, 1H) | c |
| 129 | 1.31(s, 9H), 3.96(s, 3H), 6.91(d, 1H), 7.33 (m, 1H), 7.43(d, 1H), 8.05(d, 1H), 8.36(d, 1H), 10.56(br, 1H) | c |
| 130 | 1.38(s, 9H), 3.99(s, 3H), 6.75(s, 1H), 6.95 (d, 1H), 8.07(d, 1H), 10.52(br, 1H) | c |
| 131 | 1.33(s, 9H), 3.98(s, 3H), 6.65(s, 1H), 6.94 (d, 1H), 8.06(d, 1H) | c |
| 132 | 2.24(s, 3H), 3.94(s, 3H), 5.09(s, 2H), 6.76 (d, 1H), 7.09(d, 1H), 7.18–7.55(m, 8H), 8.37 (d, 1H), 10.04(br, 1H) | c |

The invention claimed is:

1. A picolinamide compound represented by formula (1) or a salt thereof:

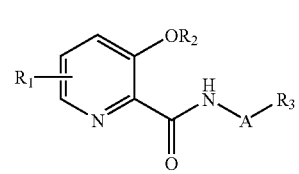

(1)

wherein

A represents a bond, an alkylene chain having 1 to 12 carbon atoms, or 2,5-dichloro-1,5-pentyl;

$R_1$ represents one or more groups, which may be the same or different, selected from the group consisting of alkoxy and haloalkoxy;

$R_2$ represents a hydrogen atom, benzyl, alkyl or alkanoyl, wherein the benzyl group may be substituted by nitro or methoxy, and the alkyl group may be substituted by methoxy or methoxyethoxy; and $R_3$ represents a hydrogen atom, cycloalkyl, cycloalkenyl, aryl or a heterocyclic group selected from the group consisting of furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolinyl, pyrimidinyl, pyridazinyl, pyrazinyl, oxiranyl, tetrahydrofuryl, perhydropyranyl, pyrrolidinyl, piperidnyl, homopiperidinyl and morpholinyl, wherein the cycloalkyl or cycloalkenyl may be substituted by one, two or more groups selected from the group consisting of a halogen atom, cyano, nitro, amino, carboxyl, hydroxyl, phenyl which may be substituted by one, two or more substituents selected from the group consisting of a halogen atom, cyano, nitro, amino, alkylamino, alkanoylamino, alkyl having 1 to 5 carbon atoms, haloalkyl having 1 to 4 carbon atoms, alkoxy having 1 to 4 carbon atoms, and haloalkoxy having 1 to 4 carbon atoms, alkyl having 1 to 5 carbon atoms, haloalkyl having 1 to 4 carbon atoms and haloalkoxy having 1 to 4 carbon atoms, and wherein the aryl or heterocyclic group may be substituted by one or two or more groups selected from the group consisting of:

a halogen atom, cyano, nitro, amino, hydroxyl, formyl, carboxyl, carbamoyl or thiocarbamoyl;

alkyl, alkoxy, alkylthio, alkylsulfinyl, or alkylsulfonyl, wherein said groups are straight-chain or branched groups having 1 to 6 carbon atoms;

straight-chain or branched $C_2$–$C_6$ alkenyl or straight-chain or branched $C_2$–$C_6$ alkenyloxy;

haloalkyl, haloalkoxy, haloalkylthio, haloalkylsulfinyl or haloalkylsulfonyl, wherein said groups are straight-chain or branched groups having 1 to 6 carbon atoms that each have 1 to 13 halogen atoms which may be the same or different;

straight-chain or branched $C_2$–$C_6$ haloalkenyloxy or straight-chain or branched $C_2$–$C_6$ haloalkenyloxy, wherein said groups each have 1 to 11 halogen atoms which may be the same or different;

acylamino, N-acyl-N-alkylamino, alkylamino, dialkylamino, alkylcarbonyl, alkylcarbonyloxy, alkoxycarbonyl, alkylsulfonyloxy, hydroxyiminoalkyl, or alkoxyiminoalkyl, wherein said groups each have straight-chain or branched alkyl having 1 to 6 carbon atoms;

alkylene, dioxyalkylene or polyoxaalkylene, wherein said groups may be substituted by one, two or more substituents selected from the group consisting of a halogen atom, straight-chain or branched alkyl having 1 to 4 carbon atoms, straight-chain or branched haloalkyl having 1 to 5 carbon atoms, which has 1 to 11 halogen atoms which may be the same or different, and are present as a chain which is substituted in its both ends at adjacent positions on the ring to form a ring; and cycloalkyl having 3 to 6 carbon atoms, aryl, aryloxy, arylthio, arylsulfinyl, arylsulfonyl, arylamino, arylalkyl, arylalkyloxy, aryloxyalkyloxy, arylthioalkyloxy, aryloxyalkylthio, arylthioalkylthio, arylalkylthio, aryloxyalkyl, arylthioalkyl, heterocyclic group, heterocyclic oxy, heterocyclic thio, heterocyclic alkyl, heterocyclic alkyloxy or heterocyclic alkylthio, wherein alkyl is straight-chain or branched alkyl having 1 to 5 carbon atoms.

2. The picolinamide compound or salt thereof according to claim 1, wherein
$R_1$ is alkoxy having 1 to 4 carbon atoms or haloalkoxy having 1 to 4 carbon atoms;
$R_2$ is alkyl having 1 to 4 carbon atoms or alkanoyl having 1 to 4 carbon atoms;
$R_3$ is cycloalkyl having 3 to 12 carbon atoms, cycloalkenyl having 3 to 12 carbon atoms, monocyclic or polycyclic 3- to 12-membered aryl or 3- to 12-membered heterocyclic group.

3. The picolinamide compound or salt thereof according to claim 1 or 2, wherein A is selected from the group consisting of a bond, methylene chain, 1,1- or 1,2-ethylene chain, 1,1-, 1,2-, 1,3-, or 2,2-propylene chain, 2-methyl-1,3-propylene chain, 1,1-, 1,2-, 1,3-, 1,4-, 2,2-, 2,3-, or 2,4-butylene chain, 3,3-dimethyl-1,4-butylene chain, 1,1,3,3-tetramethyl-1,4-butylene chain, hexamethylene chain, heptamethylene chain, octamethylene chain, nonamethylene chain, decamethylene chain, undecamethylene chain, dodecamethylene chain, 1,5-pentyl chain and 2,5-dichloro-1,5-pentyl chain.

4. The picolinamide compound or salt thereof according to claim 1, wherein $R_1$ is methoxy, ethoxy, 1-propyloxy, isopropyloxy, 1-butyloxy, 2-butyloxy, t-butyloxy, and $R_1$ is trifluoromethoxy, difluoromethoxy, fluoromethoxy, difluorochloromethoxy or trifluoroethoxy.

5. The picolinamide compound or salt thereof according to claim 1, wherein $R_1$ represents 4-methoxy, 6-methoxy, 4,5-dimethoxy, or 4,6-dimethoxy.

6. The picolinamide compound or salt thereof according to claim 1, wherein $R_2$ is p-nitrobenzyl, p-methoxybenzyl, methoxymethyl, methoxyethoxymethyl, isobutyryl, acetyl, propionyl, or pivaloyl.

7. The picolinamide compound or salt thereof according to claim 1, wherein $R_2$ represents a hydrogen atom, benzyl, acetyl or propionyl.

8. The picolinamide compound or salt thereof according to claim 1, wherein $R_3$ is cyclopropyl, cyclobutyl, cyclopentyl, cyclohexyl, cycloheptyl, cyclooctyl, cyclononyl, cyclodecyl, cycloundecyl, cyclododecyl, cyclohexenyl, tetrahydronaphthyl, decahydronaphthyl, cyclododeca-trienyl, indanyl, norbornyl, or adamantyl.

9. The picolinamide compound or salt thereof according to claim 1, wherein $R_3$ is phenyl, or naphthyl.

10. The picolinamide compound or salt thereof according to claim 1, wherein $R_3$ is an aryl or heterocyclic group substituted by a substituent selected from cycloalkyl having 3 to 6 carbon atoms, aryl, aryloxy, arylthio, arylsulfinyl, arylsulfonyl, arylamino, arylalkyl, arylalkyloxy, aryloxyalkyloxy, arylthioalkyloxy, aryloxyalkylthio, arylthioalkylthio, arylalkylthio, aryloxyalkyl, arylthioalkyl, heterocyclic group, heterocyclic oxy, heterocyclic thio, heterocyclic alkyl, heterocyclic alkyloxy or heterocyclic alkylthio, the substituent being further substituted by one, two or more groups selected from the group consisting of:

a halogen atom, cyano, nitro, amino, hydroxyl, formyl, carboxyl, carbamoyl or thiocarbamoyl;

alkyl, alkoxy, alkylthio, alkylsulfinyl or alkylsulfonyl, wherein said groups are straight-chain or branched groups having 1 to 6 carbon atoms;

straight-chain or branched $C_2$–$C_6$ alkenyl or straight-chain or branched $C_2$–$C_6$ alkenyloxy;

haloalkyl, haloalkoxy, haloalkylthio, haloalkylsulfinyl or haloalkylsulfonyl, wherein said groups are straight-chain or branched groups having 1 to 6 carbon atoms that each have 1 to 13 halogen atoms which may be the same or different;

straight-chain or branched $C_2$–$C_6$ haloalkenyl or straight-chain or branched $C_2$–$C_6$ haloalkenyloxy, wherein said groups each have 1 to 11 halogen atoms which may be the same or different;

acylamino, N-acyl-N-alkylamino, alkylamino, dialkylamino, alkylcarbonyl, alkylcarbonyloxy, alkoxycarbonyl, alkylsulfonyloxy, hydroxyiminoalkyl or alkoxyiminoalkyl, wherein said groups each have straight-chain or branched alkyl having 1 to 6 carbon atoms;

alkylene, dioxyalkylene or polyoxaalkylene, wherein said groups may be substituted by one, two or more substituents selected from the group consisting of a halogen atom, straight-chain or branched alkyl having 1 to 4 carbon atoms, straight-chain or branched haloalkyl having 1 to 5 carbon atoms, which has 1 to 11 halogen atoms which may be the same or different, and are present as a chain which is substituted in its both ends at adjacent positions on the ring to form a ring; and cycloalkyl having 3 to 6 carbon atoms or aryl, wherein said groups may be substituted by one, two or more substituents selected from the group consisting of a halogen atom, straight-chain or branched alkyl or alkoxy having 1 to 4 carbon atoms, and straight-chain or branched haloalkyl having 1 to 5 carbon atoms that has 1 to 11 halogen atoms which may be the same or different.

11. The picolinamide compound or salt thereof according to claim 1, wherein $R_3$ is selected from the group consisting of:

a hydrogen atom, 4-phenoxyphenyl, 4-(4'-t-butylphenoxy)phenyl, 4-(3'-trifluoromethylphenoxy)phenyl, 3-phenoxyphenyl, 2-phenoxyphenyl, 4-benzylphenyl, 4-(4'-methoxyphenoxy)phenyl, 3-trifluoromethyl-4-(4'-trifluoromethylphenoxy)phenyl or 4-(4'-phenylphenoxy)phenyl;

4-(4'-methylphenoxy)phenyl or 4-(4'-methylphenoxy) phenyl;

4-(4'-methylphenoxy)-3-trifluoromethylphenyl, 3-chloro-4-phenoxyphenyl, 4-phenoxy-3-trifluoromethylphenyl, 3-methyl-4-phenoxyphenyl, or 3-methoxy-4-(4'-methylphenoxy)phenyl;

4-(2',4'-di-t-butylphenoxy)phenyl, 4-(3',5'-di-t-butylphenoxy)phenyl, 3-chloro-4-(4'-chlorophenoxy)phenyl, 3-methyl-4-(4'-methoxyphenoxy)phenyl, 1-(1-naphthyl)ethyl, 3-chloro-4-(4'-methoxyphenoxy)phenyl, 3-chloro-4-(4'-methylphenoxy)phenyl, 3-methyl-4-(4'-methylphenoxy)phenyl, 4-(4'-trifluoromethoxyphenoxy)phenyl or 4-(3'-trifluoromethoxyphenoxy)phenyl;

3-methyl-4-(4'-trifluoromethylphenoxy)phenyl, 4-(4'-methylphenoxy)-2-trifluoromethylphenyl, 2,4-di-(4'-methylphenoxy)phenyl, 4-benzyloxyphenyl, 3-benzyloxyphenyl, cyclododecyl, cyclooctyl, 1-adamantyl, 1-adamantanemethyl, 4-cyclohexylphenyl, 3,4-ethylenedioxyphenyl, 4-(4'-nitrophenoxy)phenyl, 2,6-dimethyl-4-phenoxyphenyl, 4-(4'-N-isopropylaminophenoxy)phenyl, 4-(4'-isobutyrylpiperazin-1'-yl)phenyl, 2-methylcyclohexyl, cyclopropyl, cyclopentyl, cyclobutyl, 4-(2'-phenoxyethyloxy)phenyl, 4-(3'-phenoxypropyloxy)phenyl, 4-(3'-phenylpropyloxy)phenyl, 2-pyridyl, 3-pyridyl, 4-pyridyl, phenyl, 4-methylphenyl, 4-chlorophenyl, 4-fluorophenyl, 4-t-butylphenyl, 4-neopentylphenyl, 2-fluoro-4-methylphenyl, 3,4-dichlorophenyl, 3,5-difluorophenyl, 3,5-di-t-butylphenyl, 4-trifluoromethylphenyl, 4-trifluoromethoxyphenyl, 2-phenylcyclopropyl, cyclohexyl, 1-cyclohexenyl, 4-phenetyloxyphenyl, 3-chloro-4-phenetyloxyphenyl, 4-(4'-chlorophenetyloxy)phenyl, 4-methylcyclohexyl, cycloheptyl, cyclooctyl, 3-methyl-4-(3'-trifluoromethylphenoxy)phenyl, 4-t-butyl-2-chlorophenyl, 4-t-butyl-2,6-dimethylphenyl, 5-t-butylisoxazol-3-yl, or 4-t-butylthiazol-2-yl;

4-phenylthiophenyl, 2-methoxy-4-phenoxyphenyl, 3-(3-pyridyl)phenyl, 4-phenylaminophenyl or 4-(4-morpholinyl)phenyl; and 1-benzylpiperidin-4-yl, 4-(4'-aminophenoxy)phenyl, 4-benzoylphenyl, 1-indanyl, 1,2,3,4-tetrahydronaphtho-1-yl, 1-homopiperidinyl, 2-hydroxycyclohexyl or 4-hydroxycyclohexyl.

12. A method for treating plant pathogenic fungi infectious diseases, comprising the step of applying the picolinamide compound or salt thereof according to claim 1 to agricultural and gardening plants.

13. A process for producing a picolinamide compound represented by formula (1) as defined in claim 1 or a salt thereof, which process comprises:

reacting a picolinic acid compound represented by formula (2) or a salt thereof

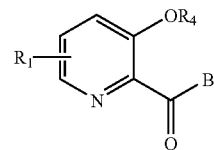

wherein

B represents hydroxyl, a halogen atom or alkoxy;

$R_1$ is as defined in claim 1; and $R_4$ represents a hydrogen atom, benzyl, alkyl having 1 to 4 carbon atoms or alkanoyl having 1 to 4 carbon atoms, in which the groups other than the hydrogen atom may be substituted by one, two or more groups selected from the group consisting of a halogen atom, cyano, nitro, amino, carboxyl, hydroxyl, phenyl which may be substituted by one, two or more substituents selected from the group consisting of a halogen atom, cyano, nitro, amino, alkylamino, alkanoylamino, alkyl having 1 to 5 carbon atoms, haloalkyl having 1 to 4 carbon atoms, alkoxy having 1 to 4 carbon atoms, and haloalkoxy having 1 to 4 carbon atoms, alkyl having 1 to 5 carbon atoms, haloalkyl having 1 to 4 carbon atoms and haloalkoxy having 1 to 4 carbon atoms, excluding the case where $R_1$ represents 4-methoxy with $R_4$ representing hydrogen or benzyl, with $H_2N$-A-$R_3$, wherein A and $R_3$ are as defined in claim 1, in an inert solvent in the presence of a condensation agent or an acid linking agent, or under aminolysis reaction conditions; and acylating the resultant reaction product.

14. The process according to claim 13, wherein B is selected from the group consisting of hydroxyl, a chlorine atom, a bromine atom, methoxy, ethoxy, methoxymethoxy, benzyloxy and 4-methoxybenzyloxy.

15. The process according to claim 13, wherein $R_1$ represents methoxy, ethoxy, 1-propyloxy, isopropoxy, 1-butyloxy, 2-butyloxy, t-butyloxy, trifluoromethoxy, difluoromethoxy, fluoromethoxy, difluorochloromethoxy or trifluoroethoxy.

16. The process according to claim 13, wherein $R_4$ represents a hydrogen atom, benzyl, p-nitrobenzyl, p-methoxybenzyl, methoxymethyl, methoxyethoxymethyl or diphenylmethyl.

17. A process for controlling deuteromyces, ascomycotina, or basidiomycetes on a plant, comprising the step of applying the picolinamide compound or salt thereof according to claim 1 to the plant.

18. A process for controlling a plant disease selected from a group consisting of rice blast, cucumber anthracnose, powdery mildew of cucumber and wheat leaf rust, comprising the step of applying the picolinamide compound or salt thereof according to claim 1 to a plant.

19. A composition comprising an anti-fungal amount of the compound according to claim 1 and an inert carrier or adjuvant.

* * * * *